(12) United States Patent
Backus et al.

(10) Patent No.: US 9,901,445 B2
(45) Date of Patent: Feb. 27, 2018

(54) VALVE LOCKING MECHANISM

(71) Applicant: BOSTON SCIENTIFIC SCIMED INC., Maple Grove, MN (US)

(72) Inventors: Andrew J. H. Backus, Santa Cruz, CA (US); Spencer C. Noe, Santa Cruz, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/944,872

(22) Filed: Nov. 18, 2015

(65) Prior Publication Data
US 2016/0143731 A1    May 26, 2016

Related U.S. Application Data

(60) Provisional application No. 62/082,946, filed on Nov. 21, 2014.

(51) Int. Cl.
*A61F 2/24*    (2006.01)

(52) U.S. Cl.
CPC ............ *A61F 2/2412* (2013.01); *A61F 2/243* (2013.01); *A61F 2/2418* (2013.01); *A61F 2/2427* (2013.01); *A61F 2220/005* (2013.01); *A61F 2220/0008* (2013.01); *A61F 2220/0033* (2013.01); *A61F 2220/0058* (2013.01)

(58) Field of Classification Search
None
See application file for complete search history.

(56) References Cited

U.S. PATENT DOCUMENTS

| 15,192 A | 6/1856 | Peale |
|---|---|---|
| 2,682,057 A | 6/1954 | Lord |

(Continued)

FOREIGN PATENT DOCUMENTS

| CN | 1338951 A | 3/2002 |
|---|---|---|
| DE | 19532846 A1 | 3/1997 |

(Continued)

OTHER PUBLICATIONS

US 8,062,356, 11/2011, Salahieh et al. (withdrawn)

(Continued)

*Primary Examiner* — Thomas J Sweet
*Assistant Examiner* — Megan Wolf
(74) *Attorney, Agent, or Firm* — Seager, Tufte and Wickhem LLP

(57) ABSTRACT

A valve replacement implant may include an expandable anchor member having a proximal end and a distal end, the anchor member being actuatable between a delivery configuration and a deployed configuration. A plurality of locking mechanisms may be configured to secure the anchor member in the deployed configuration. Each locking mechanism may include an axially movable post including a leg portion extending inwardly therefrom, and a receiving portion fixed to the anchor member, the receiving portion being configured to slidably receive the post. A plurality of valve leaflets may be disposed within a central lumen of the anchor member, the plurality of valve leaflets being secured to the leg portions of the plurality of locking mechanisms. The plurality of locking mechanisms may be releasably attached to a delivery device.

19 Claims, 16 Drawing Sheets

(56) References Cited

U.S. PATENT DOCUMENTS

| | | |
|---|---|---|
| 2,701,559 A | 2/1955 | Cooper |
| 2,832,078 A | 4/1958 | Williams |
| 3,099,016 A | 7/1963 | Edwards |
| 3,113,586 A | 12/1963 | Edmark, Jr. |
| 3,130,418 A | 4/1964 | Head et al. |
| 3,143,742 A | 8/1964 | Cromie |
| 3,334,629 A | 8/1967 | Cohn |
| 3,367,364 A | 2/1968 | Cruz, Jr. et al. |
| 3,409,013 A | 11/1968 | Berry |
| 3,445,916 A | 5/1969 | Schulte |
| 3,540,431 A | 11/1970 | Mobin-Uddin |
| 3,548,417 A | 12/1970 | Kischer et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Van Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Komberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | Dipisa, Jr. |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,483 A | 6/1993 | Tower |
| 5,238,004 A | 8/1993 | Sahatjian et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,500,014 A | 3/1996 | Quijano et al. |
| 5,507,767 A | 4/1996 | Maeda et al. |
| 5,534,007 A | 7/1996 | St Germain et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |

(56) References Cited

U.S. PATENT DOCUMENTS

| | | |
|---|---|---|
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,772,609 A | 6/1998 | Nguyen et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,051,014 A | 4/2000 | Jang |
| 6,059,827 A | 5/2000 | Fenton, Jr. |
| 6,074,418 A | 6/2000 | Buchanan et al. |
| 6,093,203 A | 7/2000 | Uflacker |
| 6,096,074 A | 8/2000 | Pedros |
| 6,123,723 A | 9/2000 | Konya et al. |
| 6,132,473 A | 10/2000 | Williams et al. |
| 6,139,510 A | 10/2000 | Palermo |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsuigita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | De Paulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,402,736 B1 | 6/2002 | Brown et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Don Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,803 B1 | 1/2003 | Horikawa et al. |
| 6,508,833 B1 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,569,196 B1 | 5/2003 | Vesely |

(56) References Cited

U.S. PATENT DOCUMENTS

| | | |
|---|---|---|
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford, III et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,769,434 B2 | 8/2004 | Liddicoat et al. |
| 6,773,454 B2 | 8/2004 | Wholey et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,814,746 B2 | 11/2004 | Thompson et al. |
| 6,821,297 B2 | 11/2004 | Snyders |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,097,658 B2 | 8/2006 | Oktay |
| 7,122,020 B2 | 10/2006 | Mogul |
| 7,125,418 B2 | 10/2006 | Duran et al. |
| 7,141,063 B2 | 11/2006 | White et al. |
| 7,166,097 B2 | 1/2007 | Barbut |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,258,696 B2 | 8/2007 | Rabkin et al. |
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 | 11/2008 | Salahieh et al. |
| 7,470,285 B2 | 12/2008 | Nugent et al. |
| 7,491,232 B2 | 2/2009 | Bolduc et al. |
| 7,510,574 B2 | 3/2009 | Lê et al. |
| 7,524,330 B2 | 4/2009 | Berreklouw |
| 7,530,995 B2 | 5/2009 | Quijano et al. |
| 7,544,206 B2 | 6/2009 | Cohn |
| 7,622,276 B2 | 11/2009 | Cunanan et al. |
| 7,628,803 B2 | 12/2009 | Pavcnik et al. |
| 7,632,298 B2 | 12/2009 | Hijlkema et al. |
| 7,674,282 B2 | 3/2010 | Wu et al. |
| 7,712,606 B2 | 5/2010 | Salahieh et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |
| 7,846,204 B2 | 12/2010 | Letac et al. |
| 7,892,292 B2 | 2/2011 | Stack et al. |
| 7,918,880 B2 | 4/2011 | Austin |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |

(56) References Cited

U.S. PATENT DOCUMENTS

| | | |
|---|---|---|
| 8,136,659 B2 | 3/2012 | Salahieh et al. |
| 8,157,853 B2 | 4/2012 | Laske et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,308,798 B2 | 11/2012 | Pintor et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson, IV et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |

(56) References Cited

U.S. PATENT DOCUMENTS

| | | |
|---|---|---|
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167619 A1* | 8/2004 | Case ............... A61F 2/2418 623/1.34 |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | Wasdyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0082165 A1 | 4/2008 | Wilson et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0269878 A1 | 10/2008 | Iobbi |
| 2008/0288054 A1 | 11/2008 | Pulnev et al. |
| 2009/0005863 A1 | 1/2009 | Goetz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |
| 2009/0093877 A1 | 4/2009 | Keidar et al. |
| 2009/0171456 A1 | 7/2009 | Kveen et al. |
| 2009/0222076 A1 | 9/2009 | Figulla et al. |
| 2009/0264759 A1 | 10/2009 | Byrd |
| 2009/0264997 A1 | 10/2009 | Salahieh et al. |
| 2009/0299462 A1 | 12/2009 | Fawzi et al. |

(56) References Cited

U.S. PATENT DOCUMENTS

| | | |
|---|---|---|
| 2010/0049313 A1 | 2/2010 | Alon et al. |
| 2010/0094399 A1 | 4/2010 | Dorn et al. |
| 2010/0121434 A1 | 5/2010 | Paul et al. |
| 2010/0191326 A1 | 7/2010 | Alkhatib |
| 2010/0219092 A1 | 9/2010 | Salahieh et al. |
| 2010/0280495 A1 | 11/2010 | Paul et al. |
| 2011/0257735 A1 | 10/2011 | Salahieh et al. |
| 2011/0276129 A1 | 11/2011 | Salahieh et al. |
| 2012/0016469 A1 | 1/2012 | Salahieh et al. |
| 2012/0016471 A1 | 1/2012 | Salahieh et al. |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0132547 A1 | 5/2012 | Salahieh et al. |
| 2012/0197379 A1 | 8/2012 | Laske et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0030520 A1 | 1/2013 | Lee et al. |
| 2013/0123796 A1 | 5/2013 | Sutton et al. |
| 2013/0158656 A1 | 6/2013 | Sutton et al. |
| 2013/0166017 A1 | 6/2013 | Cartledge et al. |
| 2013/0190865 A1 | 7/2013 | Anderson |
| 2013/0304199 A1 | 11/2013 | Sutton et al. |
| 2013/0310917 A1 | 11/2013 | Richter et al. |
| 2013/0338766 A1 | 12/2013 | Hastings et al. |
| 2014/0018911 A1 | 1/2014 | Zhou et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0243967 A1 | 8/2014 | Salahieh et al. |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0144167 B1 | 11/1989 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1088529 A2 | 4/2001 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1430853 A2 | 6/2004 |
| EP | 1472996 A1 | 11/2004 |
| EP | 1229864 B1 | 4/2005 |
| EP | 1059894 B1 | 7/2005 |
| EP | 1078610 B1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1469797 B1 | 11/2005 |
| EP | 1600121 A1 | 11/2005 |
| EP | 1156757 B1 | 12/2005 |
| EP | 1616531 A2 | 1/2006 |
| EP | 1605871 B1 | 7/2008 |
| EP | 2537487 A1 | 12/2012 |
| FR | 2788217 A1 | 7/2000 |
| GB | 2056023 A | 3/1981 |
| GB | 2398245 A | 8/2004 |
| SU | 1271508 A1 | 11/1986 |
| SU | 1371700 A1 | 2/1988 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9829057 A1 | 7/1998 |
| WO | 9836790 A1 | 8/1998 |
| WO | 9850103 A1 | 11/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 0009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0149213 A2 | 7/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0197715 A1 | 12/2001 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 02056955 A2 | 7/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03028592 A2 | 4/2003 |
| WO | 03030776 A2 | 4/2003 |
| WO | 03037227 A2 | 5/2003 |
| WO | 03047648 A2 | 6/2003 |
| WO | 03015851 B1 | 11/2003 |
| WO | 03094793 A1 | 11/2003 |
| WO | 03094797 A1 | 11/2003 |
| WO | 2004006803 A1 | 1/2004 |
| WO | 2004006804 A1 | 1/2004 |
| WO | 2004014256 A1 | 2/2004 |
| WO | 2004019811 A2 | 3/2004 |
| WO | 2004019817 A1 | 3/2004 |
| WO | 2004021922 A2 | 3/2004 |
| WO | 2004023980 A2 | 3/2004 |
| WO | 2004026117 A2 | 4/2004 |
| WO | 2004041126 A1 | 5/2004 |
| WO | 2004043293 A2 | 5/2004 |
| WO | 2004047681 A1 | 6/2004 |
| WO | 2004058106 A2 | 7/2004 |
| WO | 2004066876 A2 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |

(56) References Cited

FOREIGN PATENT DOCUMENTS

| WO | 2005009285 A2 | 2/2005 |
|---|---|---|
| WO | 2005011534 A1 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005062980 A2 | 7/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2006138391 A2 | 12/2006 |
| WO | 2007033093 A2 | 3/2007 |
| WO | 2007035471 A2 | 3/2007 |
| WO | 2007044285 A2 | 4/2007 |
| WO | 2007053243 A2 | 5/2007 |
| WO | 2007058847 A2 | 5/2007 |
| WO | 2007092354 A2 | 8/2007 |
| WO | 2007097983 A2 | 8/2007 |
| WO | 2010042950 A2 | 4/2010 |
| WO | 2012116368 A2 | 8/2012 |

OTHER PUBLICATIONS

US 8,062,357, 11/2011, Salahieh et al. (withdrawn)
US 8,075,614, 12/2011, Salahieh et al. (withdrawn)
US 8,133,271, 03/2012, Salahieh et al. (withdrawn)
US 8,211,170, 07/2012, Paul et al. (withdrawn)
Andersen et al., "Transluminal implantation of artificial heart valves. Description of a new expandable aortic valve and initial results with implantation by catheter technique in closed chest pigs." Euro. Heart J., 13:704-708, 1992.
Atwood et al., "Insertion of Heart Valves by Catheterization." Project Supervised by Prof. S. Muftu of Northeastern University 2001-2002: 36-40.
Bodnar et al., "Replacement Cardiac Valves R Chapter 13: Extinct Cardiac Valve Prostheses" Pergamon Publishing Corporation. New York, 1991: 307-322.
Boudjemline et al., "Percutaneous Implantation of a Biological Valve in the Aorta to Treat Aortic Valve Insufficiency—A Sheep Study." Med Sci. Monit., vol. 8, No. 4: BR113-116, 2002.
Boudjemline et al., "Percutaneous Implantation of a Valve in the Descending Aorta in Lambs." Euro. Heart J., 23: 1045-1049, 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, 2004.
Boudjemline et al., "Percutaneous Valve Insertion: A New Approach?" J. of Thoracic and Cardio. Surg, 125(3): 741-743, 2003.
Boudjemline et al., "Steps Toward Percutaneous Aortic Valve Replacement." Circulation, 105: 775-778, 2002.
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, 2004.
Cribier et al., "Percutaneous Transcatheter Implementation of an Aortic Valve Prosthesis for Calcific Aortic Stenosis: First Human Case Description." Circulation, 106: 3006-3008, 2002.
Cribier et al., "Percutaneous Transcatheter Implantation of an Aortic Valve Prosthesis for Calcific Aortic Stenosis: First Human Case." Percutaneous Valve Technologies, Inc., 16 pages, 2002.
Ferrari et al., "Percutaneous Transvascular Aortic Valve Replacement with Self-Expanding Stent-Valve Device." Poster from the presentation given at SMIT 2000, 12th International Conference. Sep. 5, 2000.
Hijazi, "Transcatheter Valve Replacement: A New Era of Percutaneous Cardiac Intervention Begins." J. of Am. College of Cardio., 43(6): 1088-1089, 2004.
Huber et al., "Do Valved Stents Compromise Coronary Flow?" European Journal of Cardio-thoracic Surgery, vol. 25: 754-759, 2004.
Knudsen et al., "Catheter-implanted prosthetic heart valves." Int'l J. of Art. Organs, 16(5): 253-262, 1993.
Kort et al., "Minimally Invasive Aortic Valve Replacement: Echocardiographic and Clinical Results." Am. Heart J., 142(3): 476-481, 2001.
Love et al., The Autogenous Tissue Heart Valve: Current Status. Journal of Cardiac Surgery, 6(4): 499-507, 1991.
Lutter et al., "Percutaneous Aortic Valve Replacement: An Experimental Study. I. Studies on Implantation." J. of Thoracic and Cardio. Surg., 123(4): 768-776, 2002.
Moulopoulos et al., "Catheter-Mounted Aortic Valves." Annals of Thoracic Surg., 11(5): 423-430, 1971.
Paniagua et al., "Percutaneous Heart Valve in the Chronic in Vitro Testing Model." Circulation, 106: e51-e52, 2002.
Paniagua et al., "Heart Watch." Texas Heart Institute. Spring, 2004. Edition: 8 pages.
Pavcnik et al., "Percutaneous Bioprosthetic Veno Valve: A Long-term Study in Sheep." J. of Vascular Surg., 35(3): 598-603, 2002.
Phillips et al., "A Temporary Catheter-Tip Aortic Valve: Hemodynamic Effects on Experimental Acute Aortic Insufficiency." Annals of Thoracic Surg., 21(2): 134-136, 1976.
Sochman et al., "Percutaneous Transcatheter Aortic Disc Valve Prosthesis Implantation: A Feasibility Study." Cardiovasc. Intervent. Radiol., 23: 384-388, 2000.
Stuart, "In Heart Valves, A Brave, New Non-Surgical World." Start-Up. 9-17, 2004.
Vahanian et al., "Percutaneous Approaches to Valvular Disease." Circulation, 109: 1572-1579, 2004.
Van Herwerden et al., "Percutaneous Valve Implantation: Back to the Future?" Euro. Heart J., 23(18): 1415-1416, 2002.
Zhou et al, "Self-expandable Valved Stent of Large Size: Off-Bypass Implantation in Pulmonary Position." Eur. J. Cardiothorac, 24: 212-216, 2003.
"A Matter of Size." Treiennial Review of the National Nanotechnology Initiative, The National Academies Press, Washington DC, v-13, 2006, http://www.nap.edu/catalog/11752/a-matter-of-size-triennial-review-of-the-national-nanotechnology.
Atwood et al., "Insertion of Heart Valves by Catheterization." The Capstone Design Course Report. MIME 1501-1502. Technical Design Report Northeastern University, pp. 1-93, Nov. 5, 2007.
Aug. 19, 2011, Supplemental Search Report from EP Patent Office, EP Application No. 04813777.2.
Aug. 19, 2011, Supplemental Search Report from EP Patent Office, EP Application No. 04815634.3.
Cunanan et al., "Tissue Characterization and Calcification Potential of Commerical Bioprosthetic Heart Valves." Ann. Thorac. Surg., S417-421, 2001.
Cunliffe et al., "Glutaraldehyde Inactivation of Exotic Animal Viruses in Swine Heart Tissue." Applied and Environmental Microbiology, Greenport, New York, 37(5): 1044-1046, May 1979.
EP Search Report dated Aug. 10, 2011 for EP Application No. 06824992.9.
"Heart Valve Materials—Bovine (cow)." Equine & Porcine Pericardium, Maverick Biosciences Pty. Lt, http://maverickbio.com/biological-medical-device-materials.php?htm. 2009.
Helmus, "Mechanical and Bioprosthetic Heart Valves in Biomaterials for Artificial Organs." Woodhead Publishing Limited: 114-162, 2011.
Hourihan et al., "Transcatheter Umbrella Closure of Valvular and Paravalvular Leaks." JACC, Boston, Massachusetts, 20(6): 1371-1377, Nov. 15, 1992.
Laborde et al., "Percutaneous Implantation of the Corevalve Aortic Valve Prosthesis for Patients Presenting High Risk for Surgical Valve Replacement." EuroIntervention: 472-474, 2006.
Levy, "Mycobacterium Chelonei Infection of Porcine Heart Valves." The New England Journal of Medicine, Washington DC, 297(12), Sep. 22, 1977.

(56) References Cited

OTHER PUBLICATIONS

Supplemental Search Report from EP Patent Office, EP Application No. 05758878.2, dated Oct. 24, 2011.
"Pericardial Heart Valves." Edwards Lifesciences, Cardiovascular Surgery FAQ, Nov. 14, 2010, http://www.edwards.com/products/cardiovascularsurgeryfaq.htm.
Southern Lights Biomaterials Homepage, Jan. 7, 2011, http://www.slv.co.nz/.
Stassano. "Mid-term Results of the Valve-on-Valve Technique for Bioprosthetic Failure." European Journal of Cardiothoracic Surgery: 453-457, 2000.
PCT Application No. US2015/061954, The International Search Report and Written Opinion of the International Searching Authority, dated Feb. 22, 2016, 11 pages.
Examiner's First Report on AU Patent Application No. 2011202667, dated May 17, 2012.
Topol. "Percutaneous Expandable Prosthetic Valves." Textbook of Interventional Cardiology, W.B. Saunders Company, 2: 1268-1276, 1994.

* cited by examiner

VALVE LOCKING MECHANISM

CROSS-REFERENCE TO RELATED APPLICATIONS

This application claims the benefit of U.S. Provisional Application No. 62/082,946, filed Nov. 21, 2014.

TECHNICAL FIELD

The present disclosure pertains to medical devices, and methods for manufacturing and/or using medical devices. More particularly, the present disclosure pertains to locking mechanisms for a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

In a first aspect, a valve replacement implant may include an expandable anchor member having a proximal end and a distal end, the anchor member being actuatable between a delivery configuration and a deployed configuration. The valve replacement implant may include a plurality of locking mechanisms configured to secure the anchor member in the deployed configuration, each locking mechanism including: an axially movable post including a leg portion extending inwardly therefrom; and a receiving portion fixed to the anchor member, the receiving portion being configured to slidably receive the post. The valve replacement implant may include a plurality of valve leaflets disposed within a central lumen of the anchor member, the plurality of valve leaflets being secured to the leg portions of the plurality of locking mechanisms, wherein the plurality of locking mechanisms is releasably attached to a delivery device.

In addition or alternatively, and in a second aspect, the leg portion extends from the post toward the proximal end.

In addition or alternatively, and in a third aspect, the leg portion is attached to the post at a distal end of the post.

In addition or alternatively, and in a fourth aspect, the leg portion is flexibly attached to the post.

In addition or alternatively, and in a fifth aspect, the leg portion includes a free end and a secured end, the leg portion being attached to the post at the secured end.

In addition or alternatively, and in a sixth aspect, the free end is unattached to any other structure except through the leg portion.

In addition or alternatively, and in a seventh aspect, at least part of the leg portion longitudinally overlaps the receiving portion along a central longitudinal axis of the anchor member in the deployed configuration.

In addition or alternatively, and in an eighth aspect, the plurality of valve leaflets is secured directly to the leg portions.

In addition or alternatively, and in a ninth aspect, the plurality of valve leaflets is not directly secured to the posts.

In addition or alternatively, and in a tenth aspect, the anchor member is actuated between the delivery configuration and the deployed configuration by translating the post proximally relative to the receiving portion.

In addition or alternatively, and in an eleventh aspect, the post includes two leg portions extending inwardly therefrom.

In addition or alternatively, and in a twelfth aspect, the two leg portions are joined together at a free end opposite the post.

In addition or alternatively, and in a thirteenth aspect, the two leg portions are arranged generally parallel to each other.

In addition or alternatively, and in a fourteenth aspect, at least some of the plurality of valve leaflets pass between the two leg portions.

In addition or alternatively, and in a fifteenth aspect, the at least some of the plurality of valve leaflets passing between the two leg portions wrap around the two leg portions.

In addition or alternatively, and in a sixteenth aspect, the at least some of the plurality of valve leaflets passing between the two leg portions and wrapping around the two leg portions are secured back to themselves.

In addition or alternatively, and in a seventeenth aspect, the at least some of the plurality of valve leaflets are secured back to themselves using one or more sutures.

In addition or alternatively, and in an eighteenth aspect, the at least some of the plurality of valve leaflets are secured back to themselves using an adhesive.

In addition or alternatively, and in a nineteenth aspect, a distalmost end of the post is coupled to the distal end of the anchor member.

In addition or alternatively, and in a twentieth aspect, a distalmost end of the plurality of valve leaflets is coupled to the distal end of the anchor member.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
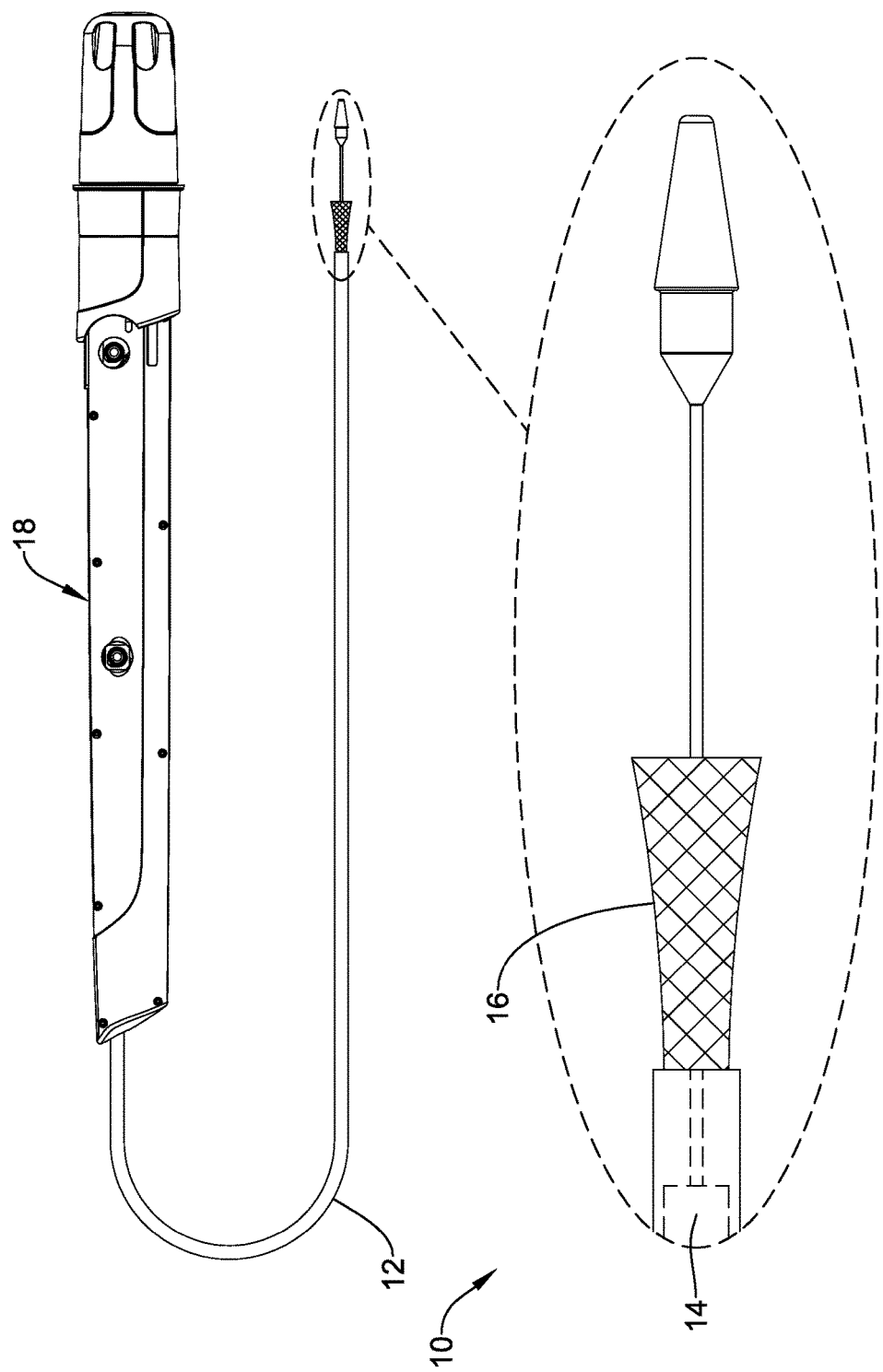
FIG. 1 is a schematic side view of an example medical device system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally be considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve can have a serious effect on a human and could lead to serious health condition and/or death if not dealt with. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve). In addition, the devices disclosed herein may deliver the replacement heart valve percutaneously and, thus, may be much less invasive to the patient. The devices disclosed herein may also provide a number of additional desirable features and benefits as described in more detail below.

FIG. 1 is a side view of an example medical device system 10. It should be noted that some features of the medical device system 10 are either not shown, or are shown schematically, in FIG. 1 for simplicity. Additional details regarding some of the components of the medical device system 10 are provided in other figures in greater detail. A medical device system 10 may be used to deliver and/or deploy a variety of medical devices to a number of locations within the anatomy. In at least some embodiments, the medical device system 10 may be a replacement heart valve delivery system (e.g., a replacement aortic valve delivery system) that can be used for percutaneous delivery of a replacement heart valve. This, however, is not intended to be limiting as the medical device system 10 may also be used for other interventions including mitral valve replacement, valve repair, valvuloplasty, and the like, or other similar interventions.

The medical device system 10 may generally be described as a catheter system that includes a catheter or an outer sheath 12 and a tube or an inner catheter 14 (a portion of which is shown in FIG. 1 in phantom line) slidably extending at least partially through the outer sheath 12. A medical implant 16 (i.e., a valve replacement implant, for example) may be coupled to the inner catheter 14 and disposed within a lumen of the outer sheath 12 during delivery of the medical implant 16. A handle 18 may be disposed at a proximal end of the outer sheath 12 and/or the inner catheter 14. In general, the handle 18 may be configured to manipulate the position of the outer sheath 12 relative to the inner catheter 14, as well as aid in the deployment of the medical implant 16.

Figure 2:
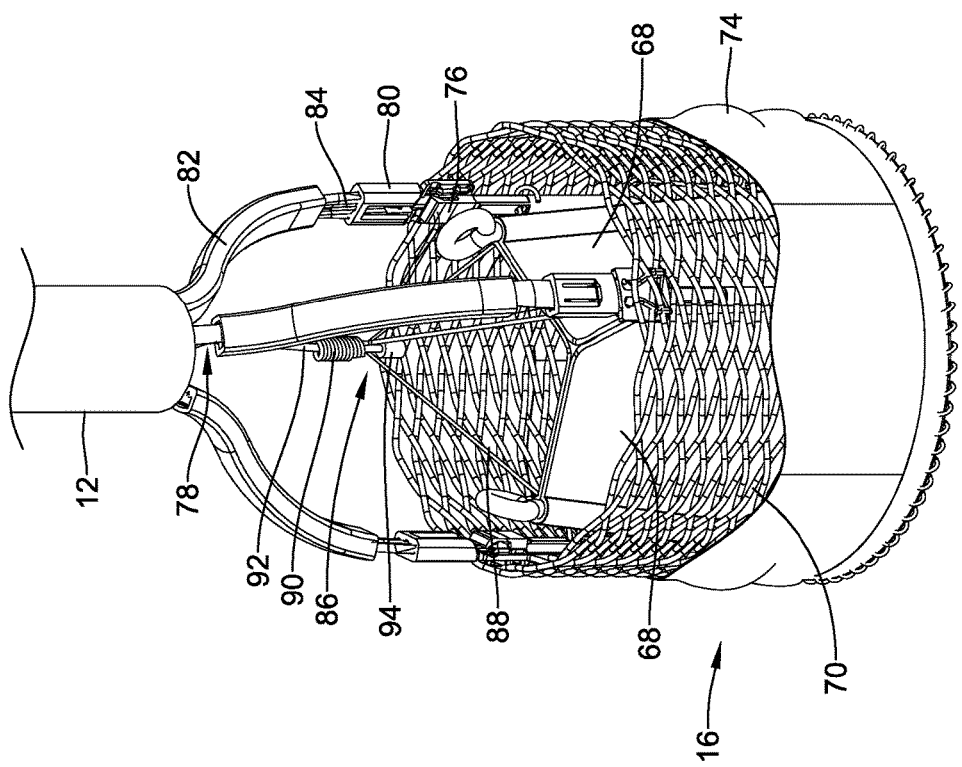
FIG. 2 is a perspective view of a portion of an example implant associated with the example medical device system in a deployed configuration.

In use, the medical device system 10 may be advanced percutaneously through the vasculature to a position adjacent to an area of interest. For example, the medical device system 10 may be advanced through the vasculature and across the aortic arch to a position adjacent to a defective aortic valve (or other heart valve). During delivery, the medical implant 16 may be generally disposed in an elongated and low profile "delivery" configuration within the outer sheath 12 (as partially shown in FIG. 1, for example). Once positioned, the outer sheath 12 may be retracted to expose the medical implant 16. The medical implant 16 may be actuated in order to radially expand the medical implant 16 into a generally shortened and larger profile "deployed" configuration suitable for implantation within the anatomy (as shown in FIG. 2, for example). When the medical implant 16 is suitably deployed within the anatomy, the medical device system 10 can be removed from the vasculature, leaving the medical implant 16 in place in a "released" configuration to function as, for example, a suitable replacement for the native aortic valve. In at least some interventions, the medical implant 16 may be deployed within the native valve (e.g., the native valve is left in place and not excised). Alternatively, the native valve may be removed and the medical implant 16 may be deployed in its place as a replacement.

In some embodiments, the outer sheath 12 may have a proximal portion and a distal portion. In some embodiments, the distal portion may have a slightly enlarged or flared inner diameter, which may provide additional space for holding the medical implant 16 therein. For example, in some embodiments, an inner diameter of outer sheath 12 along a proximal portion may be in the range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.56388±0.0508 cm (0.222±0.002 inches). In some embodiments, an inner diameter of outer sheath 12 along a distal portion may be in the range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.579 to 0.5842 cm (0.228 to 0.230 inches). At the distal end of the distal portion may be a distal tip, which may be flared or otherwise have a funnel-like shape. The funnel-like shape may increase the outer diameter (and inner diameter) of the outer sheath 12 at the distal tip and may aid in the sheathing and/or re-sheathing of the medical implant 16 into the outer sheath 12. Other than at the distal tip, the outer sheath 12 may have a generally constant outer diameter. For example, in some embodiments, the outer sheath 12 may have an outer diameter in a range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.6858 cm (0.270 inches). These are just examples. Other embodiments are contemplated that have differing dimensions (including those appropriate for differently sized patients including, but not limited to, children) and/or arrangements for the outer diameter and/or inner diameter of the outer sheath 12. These contemplated embodiments include outer sheaths with flared or otherwise variable outer diameters, embodiments with constant inner diameters, combinations thereof, and the like. The outer sheath 12 may also have a length that is appropriate for reaching the intended area of interest within the anatomy. For example, the outer sheath 12 may have a length in the range of about 30 to 200 cm, or about 60 to 150 cm, or about 100 to 120 cm, or about 108±0.20 cm. In some embodiments, some, all, or a portion of the outer sheath 12 may also be curved. For example, in some embodiments, a distal section of outer sheath 12 may be curved. In one example, a radius of the curve (measured from the center of outer sheath 12) may be in the range of about 2 to 6 cm (20 to 60 mm), or about 3 to 4 cm (30 to 40 mm), or about 3.675 cm (36.75 mm). Again, these dimensions are examples and are not intended to be limiting.

In some embodiments, the outer sheath 12 may be formed from a singular monolithic tube or unitary member. Alternatively, the outer sheath 12 may include a plurality of layers or portions. In some embodiments, one or more of these layers may include a reinforcing structure such as a braid, coil, mesh, combinations thereof, or the like. In some embodiments, a reinforcement or reinforcement layer may be disposed on an intermediate layer. In some embodiments, an outer coating (e.g., a lubricious coating, a hydrophilic coating, a hydrophobic coating, etc.) may be disposed along portions or all of an outer layer. These are just examples. Other alternative structural configurations are also contemplated.

The dimensions and materials utilized for the various layers of the outer sheath 12 may also vary. For example, an inner layer may include a polymeric material such as fluorinated ethylene propylene (FEP) and may have a thickness in the range of about 0.00254 to 0.0127 cm (0.001 to 0.005 inches) or about 0.00762±0.00254 (0.003±0.001 inches), an intermediate layer may include a polymer material such as polyether block amide (e.g., PEBAX 6333) and may have a thickness in the range of about 0.00254 to 0.0127 cm (0.001 to 0.005 inches) or about 0.00508±0.00254 (0.002±0.001 inches), an outer layer may include a polymer material such as polyether block amide (e.g., PEBAX 7233) and may have a thickness in the range of about 0.00254 to 0.0254 cm (0.001 to 0.01 inches). In some embodiments, the outer layer may vary in thickness. For example, along the proximal portion, the outer layer may have greater thickness, such as about 0.0127 to about 0.0508 cm or about 0.02159 cm (0.005 to 0.02 inches or about 0.0085 inches), than along the distal portion and/or at the distal tip, which may be about 0.0127 to about 0.0508 cm or about 0.01651 cm (e.g., about 0.005 to 0.02 inches or about 0.0065 inches). These are just examples as other suitable materials may be used.

The form of the distal tip may also vary. For example, in at least some embodiments, the inner liner layer (i.e., a 2.5 mm section thereof, for example) may be extended up and around the distal end of the outer sheath 12. In some embodiments, a ring member (not shown) made from a suitable material such as a 55D polyether block amide (e.g., 55D PEBAX) may be disposed over the inner layer and heat bonded to form the distal tip. In some embodiments, this may form the funnel-like shape of the distal tip.

In some embodiments, a reinforcement or reinforcement layer may take the form of a braid, coil, mesh, or the like. For example, in some embodiments, the reinforcement or reinforcement layer may include a metallic braid (e.g., stainless steel). In some of these embodiments, the reinforcement or reinforcement layer may also include additional structures such as one or more longitudinally-extending strands. For example, the reinforcement or reinforcement layer may include a pair of longitudinally-extending aramid and/or para aramid strands (for example, KEVLAR®) disposed on opposite sides of the braid. These strands may or may not be woven into portions or all of the braid.

In some embodiments, a distal end region of the inner catheter 14 may include a stepped outer diameter that defines a decreased outer diameter section. For example, the decreased outer diameter section may have an outer diameter in a range of about 0.127 to 0.635 cm (0.05 to 0.25 inches), or about 0.254 to 0.508 cm (0.10 to 0.20 inches), or about 0.38608±0.00762 (0.152±0.003 inches) as opposed to the remainder of the inner catheter 14 where the outer diameter may be in a range of about 0.127 to 0.762 cm (0.05 to 0.30 inches), or about 0.254 to 0.635 cm (0.10 to 0.25 inches), or about 0.508±0.0254 cm (0.20±0.01 inches). In some embodiments, the decreased outer diameter section may define a region where other components of the medical device system 10 may be attached.

In general, the inner catheter 14 may take the form of an extruded polymer tube. Other forms are also contemplated including other polymer tubes, metallic tubes, reinforced tubes, or the like including other suitable materials such as those disclosed herein. In some embodiments, the inner catheter 14 is a singular monolithic or unitary member. In other embodiments, the inner catheter 14 may include a plurality of portions or segments that are coupled together. A total length of the inner catheter 14 may be in a range of about 60 to 150 cm, or about 80 to 120 cm, or about 100 to 115 cm, or about 112±0.02 cm. Just like the outer sheath 12, in some embodiments, the inner catheter 14 may also be curved, for example adjacent to a distal end thereof. In some embodiments, the inner catheter 14 may have one or more sections or regions with a differing hardness/stiffness (e.g., differing shore durometer). For example, in some embodiments, the inner catheter 14 may have a proximal region and an intermediate region. The proximal region may include a generally stiff polymeric material such as a 72D polyether block amide (e.g., 72D PEBAX) and may have a length in a range of about 60 to 150 cm, or about 80 to 120 cm, or about 100 to 115 cm, or about 109.5±0.02 cm. The intermediate region may include a 40D polyether block amide (e.g., 40D PEBAX) and may have a length in a range of about 5 to 25 mm, or about 10 to 20 mm, or about 15±0.01 mm. In some embodiments, the decreased outer diameter section may also differ from the proximal region and/or the intermediate region, and in some embodiments, may include a 72D polyether block amide (e.g., 72D PEBAX) and may have a length in the range of about 0.5 to 2 cm (5 to 20 mm), or about 0.8 to 1.5 cm (8 to 15 mm), or about 1±0.001 cm (10±0.01 mm). These are just examples.

In some embodiments, the inner catheter 14 may include one or more lumens extending therethrough. For example, in some embodiments, the inner catheter 14 may include a first lumen, a second lumen, a third lumen, and a fourth lumen. In general, the one or more lumens extend along an entire length of the inner catheter 14. Other embodiments are contemplated, however, where one or more of the one or more lumens extend along only a portion of the length of the inner catheter 14. For example, in some embodiments, the fourth lumen may stop just short of a distal end of the inner catheter 14 and/or be filled in at its distal end to effectively end the fourth lumen proximal of the distal end of the inner catheter 14.

Disposed within a first lumen of the inner catheter 14 may be at least one actuator element, such as a push-pull rod 84 for example, which may be used to actuate (i.e., expand and/or elongate) the medical implant 16 between a delivery configuration and a deployed configuration. In some cases, the push-pull rod(s) 84 may herein be referred to, or used interchangeably with, the term "actuator element". In other words, the medical device system 10 may include at least one push-pull rod 84. In some embodiments, the at least one push-pull rod 84 may include two push-pull rods 84, three push-pull rods 84, four push-pull rods 84, or another suitable or desired number of push-pull rods 84. For the purpose of illustration only, the medical device system 10 and/or the medical implant 16 is shown with three push-pull rods 84.

In at least some embodiments, the first lumen may be lined with a low friction liner (e.g., a FEP liner). Disposed within a second lumen may be a pin release mandrel 92, which is explained in more detail herein. In at least some embodiments, the second lumen may be lined with a hypotube liner. A third lumen may be a guidewire lumen and in some embodiments, the third lumen may also be lined with a hypotube liner. In some embodiments, a fourth lumen may be used to house a non-stretch wire. The form of non-stretch wire may vary. In some embodiments, the non-stretch wire may take the form of a stainless steel braid. The non-stretch wire may optionally include a pair of longitudinally-extending aramid and/or para aramid strands (for example, KEVLAR®) disposed on opposite sides of the braid. In general, rather than being "disposed within" the fourth lumen, the non-stretch wire may be embedded within the fourth lumen. In addition, the non-stretch wire may extend to a position adjacent to the distal end region but not fully to the distal end of the inner catheter 14. For example, a short distal segment of the fourth lumen may be filled in with polymer material adjacent to the distal end of the inner catheter 14.

The inner catheter 14 may also include a guidewire tube extension that extends distally from the distal end region. In some embodiments, a nose cone may be attached to the guidewire tube extension. In some embodiments, the nose cone generally is designed to have an atraumatic shape. In some embodiments, the nose cone may also include a ridge or ledge that is configured to abut the distal tip of the outer sheath 12 during delivery of the medical implant 16.

FIG. 2 illustrates some selected components of the medical device system 10 and/or the medical implant 16. For example, here it can be seen that the medical implant 16 may include a plurality of valve leaflets 68 (e.g., bovine pericardial) which may be secured to a cylindrical anchor member or braid 70 that is reversibly actuatable between a "delivery" configuration and a "deployed" configuration. In some embodiments, the medical implant 16 may include a plurality of locking mechanisms configured to secure the anchor member or braid 70 in the "deployed" configuration. In some embodiments, the at least one actuator element (i.e., the push-pull rods 84) may be configured to engage with the plurality of locking mechanisms and actuate the anchor member or braid 70 between the "delivery" configuration and the "deployed" configuration. In some embodiments, one actuator element may correspond to, engage with, and/or actuate one locking mechanism. In some embodiments, one actuator element may correspond to, engage with, and/or actuate more than one locking mechanism. Other configurations are also contemplated.

While a plurality of actuator elements and/or corresponding locking mechanisms may be included in a medical implant 16, for clarity and brevity, much of the following discussion will be limited to a single instance of these elements. The skilled person will readily recognize that the features and operation of the examples discussed below may apply equally to and across all instances of the plurality of locking mechanisms and/or actuator elements.

In some embodiments, the plurality of locking mechanisms may each comprise an axially movable post 72, for example at the commissure portions of the valve leaflets 68 (post 72 may sometimes be referred to as a "commissure post"), and a receiving portion (such as a buckle 76, for example) fixed to the anchor member or braid 70. In other words, in at least some embodiments, a medical implant 16 may include a plurality of posts 72 and a corresponding plurality of receiving portions or buckles 76. Other configurations and correspondences are also contemplated. In some embodiments, the post 72 may engage the receiving portion or buckle 76 in the "deployed" configuration. In some embodiments, the post 72 may be axially or longitudinally spaced apart from the receiving portion or buckle 76 in the "delivery" configuration.

In some embodiments, a distalmost end of the axially movable post 72 may be secured and/or attached (i.e., fixedly attached, movably attached, removably attached, etc.) to a distal portion of the anchor member or braid 70, such as by a suture, a tether, adhesives, or other suitable element. In some embodiments the post 72 may be axially or longitudinally movable relative to the anchor member or braid 70 and/or the receiving portion or buckle 76 fixed to the anchor member or braid 70. Other embodiments are contemplated where the receiving portion or buckle 76 may be movably or removably attached to the anchor member or braid 70. In some embodiments, the post 72 may be fixedly attached to the anchor member or braid 70 and the receiving portion or buckle 76 may be fixedly attached to the anchor member or braid 70. In some embodiments, one of the post 72 and the receiving portion or buckle 76 may be fixedly attached to the anchor member or braid 70 and the other may be movably or removably attached to the anchor member or braid 70. In some embodiments, the post 72 may be movably or removably attached to the anchor member or braid 70 and the receiving portion or buckle 76 may be movably or removably attached to the anchor member or braid 70. In some embodiments, the post 72 may be secured or attached (i.e., fixedly attached, movably attached, removably attached, etc.) to a distal end of the anchor member or braid 70. In some embodiments, the receiving portion or buckle 76 may be fixed or attached to a proximal portion of the anchor member or braid 70. In some embodiments, the receiving portion or buckle 76 may be fixed or attached at or to a proximal end of the anchor member or braid 70.

In some embodiments, the medical implant 16 may include one or more of the plurality of valve leaflets 68 secured to the anchor member or braid 70 at, adjacent to, and/or using (at least in part) individual, corresponding posts 72. The valve leaflets 68 may also be secured to a base, or the distal end, of the anchor member or braid 70. Positioned adjacent to (e.g., aligned with) the plurality of posts 72 is a corresponding plurality of receiving portions or buckles 76. In the illustrated examples, one receiving portion or buckle 76 is attached to the anchor member or braid 70 adjacent to each of the three posts 72. Accordingly, the anchor member or braid 70 has a total of three receiving portions or buckles 76 and three posts 72 attached thereto. Similarly, one actuating element or push-pull rod 84 may be operatively associated with each post 72 and buckle 76, for a total of three actuating elements or push-pull rods 84 in the illustrated examples. Other embodiments are contemplated where fewer or more receiving portions or buckles 76, posts 72, and actuator elements or push-pull rods 84 may be utilized. In some embodiments, a seal 74 may be disposed about the anchor member or braid 70 and, as the term suggests, may help to seal the medical implant 16 within and/or against a target implant site or area of interest upon deployment.

In some embodiments, attachment between the medical implant 16 and the inner catheter 14 (and/or the outer sheath 12) may be effected through the use of a coupler 78. In some embodiments, the coupler 78 may generally include a cylindrical base (not shown) that may be disposed about and/or attached to the inner catheter 14. Projecting distally from the base is a plurality of fingers (e.g., two, three, four, etc.) that are each configured to engage with the medical implant 16 at a proximal end of one of the receiving portions or buckles 76. A collar 80 may be disposed about the fingers of the coupler 78 to further assist in holding together the fingers and the receiving portions or buckles 76, as will be described in more detail below. A guide 82 may be disposed over each of the fingers proximal of the collar 80 and may serve to keep the fingers of the coupler 78 associated with the actuator elements or push-pull rods 84 extending adjacent to (and axially slidable relative to) the fingers of the coupler 78. Finally, a pin release assembly 86 may be a linking structure that keeps posts 72, buckles 76, and push-pull rods 84 associated with one another. In some embodiments, the pin release assembly 86 may include a plurality of individual pins 88 that may be joined together via a coiled connection 90 and held to a pin release mandrel 92 with a ferrule 94.

During delivery, the medical implant 16 may be secured at the distal end of the inner catheter 14 by virtue of the association of the fingers of the coupler 78 being coupled with a projecting proximal end of the receiving portion or buckle 76 (and being held in place with the collar 80 disposed over the connection) and by virtue of the pins 88 securing together the actuator elements or push-pull rods 84 and the posts 72, as will be described below. When the medical implant 16 is advanced to the target site or area of interest, the outer sheath 12 may be withdrawn (e.g., moved proximally relative to the inner catheter 14) to expose the medical implant 16. Then, the actuator elements or push-pull rods 84 can be used to axially shorten and/or radially expand and "lock" the medical implant 16 and/or the anchor member or braid 70 from the "delivery" configuration (as shown in FIG. 1, for example) to an expanded or "deployed" configuration (as shown in FIG. 2, for example) by proximally retracting the actuator elements or push-pull rods 84 to pull the posts 72 into engagement with the receiving portions or buckles 76. Finally, the pins 88 can be removed, thereby uncoupling the actuator elements or push-pull rods 84 from the posts 72, which allows the actuator elements or push-pull rods 84 and the fingers of the coupler 78 to be withdrawn from the medical implant 16 thereby deploying the medical implant 16 (and/or the anchor member or braid 70) in the anatomy in a "released" configuration. In other words, one difference between the "deployed" configuration and the "released" configuration is whether or not the pins 88 are attached to the posts 72. In the "deployed" configuration, the pins 88 are still attached to the posts 72, which thus permits the medical implant 16 (and/or the anchor member or braid 70) to be unlocked via distal advancement of the actuator elements or push-pull rods 84, as described further below, in order to reposition the medical implant 16, for example. In some embodiments, at least a portion of the plurality of valve leaflets 68 may axially or longitudinally overlap at least a portion of the receiving portions or buckles 76 at a common position along a central longitudinal axis of the anchor member or braid 70.

FIGS. 3-6 illustrate selected components of a locking mechanism configured to lock the medical implant 16 (and/or the anchor member or braid 70) in the "deployed" configuration, and the general operation of those components. For simplicity and clarity purposes, only one of the fingers of the coupler 78, only one of the actuator elements or push-pull rods 84, only one of the posts 72, only one of the receiving portions or buckles 76, only one of the collars 80, and only one of the pins 88 are shown and discussed (the whole medical implant 16 and/or the anchor member or braid 70 is not shown to facilitate understanding of the locking mechanisms). However, it will be understood that the following discussion may apply equally to any and/or all of the components for which there are more than one within the medical implant 16 (i.e., the actuator elements or push-pull rods 84, the receiving portions or buckles 76, the posts 72, the pins 88, etc.) and/or the medical device system 10.

As seen in FIGS. 2-6, each actuator element or push-pull rod 84 extends through a guide 82 adjacent to a finger of the coupler 78, through a receiving portion or buckle 76, and into a passage extending longitudinally into a proximal end of a hollow bar portion 96 of a post 72. The actuator element or push-pull rod 84 may be axially translatable through the receiving locking portion or buckle 76. In some embodiments, a distal portion of the actuator element or push-pull rod 84 may include a keyed orienting structure configured to slidable and non-rotatably mate with the passage extending longitudinally into the proximal end of the hollow bar portion 96 of the post 72.

Figure 3:
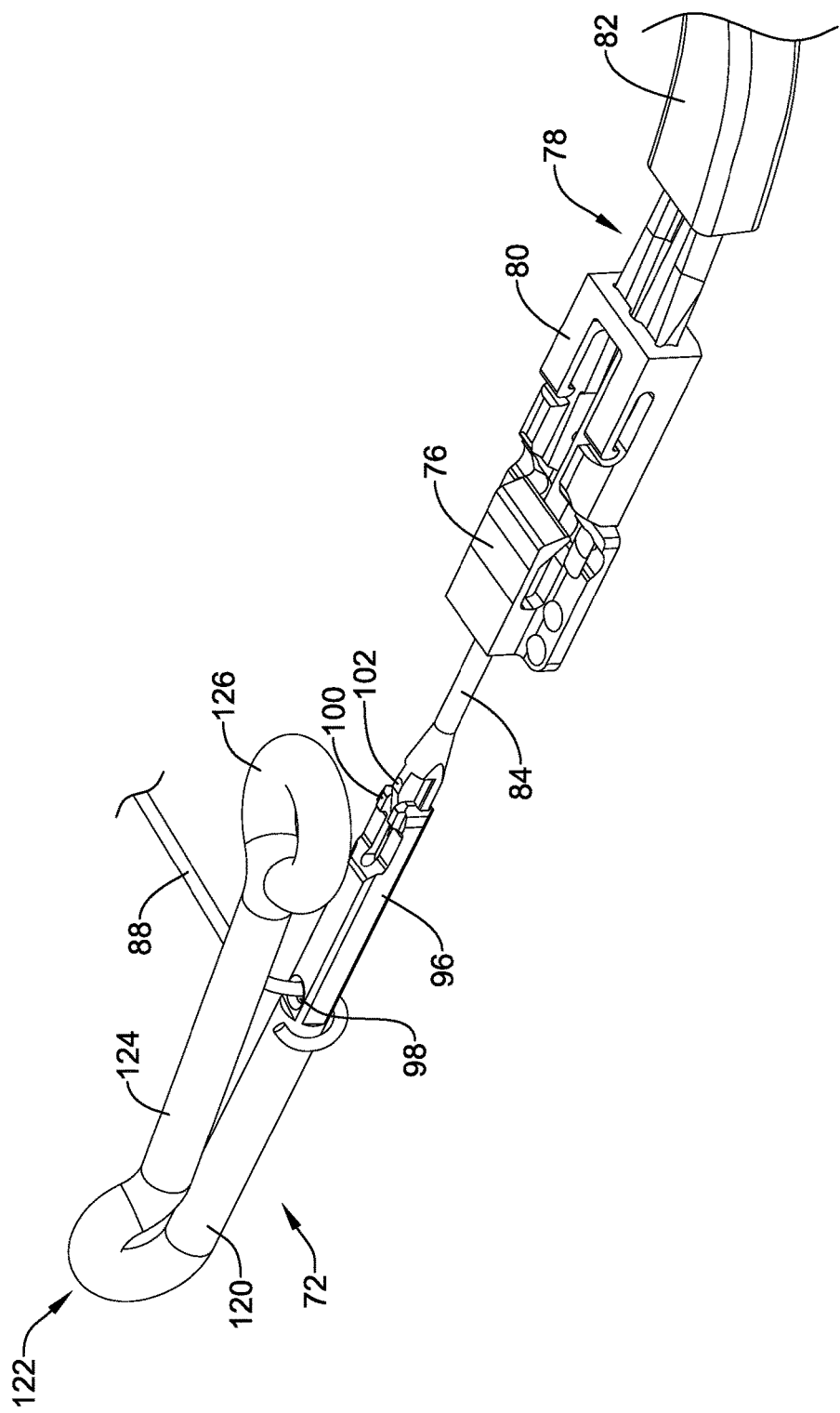
FIG. 3 illustrates selected components of an example implant associated with the example medical device system in a delivery configuration.

A distal end of the actuator element or push-pull rod 84 may include a longitudinally-oriented elongated aperture or slot (not shown) that can be aligned with an opening 98 through the bar portion 96 of the post 72. When so aligned, a pin 88 can be looped through the opening 98 and the elongated aperture or slot of the actuator element or push-pull rod 84. This releasably couples the actuator element or push-pull rod 84 to the post 72 and forms a configuration of these structures that can be utilized during delivery of the medical implant 16. As can be appreciated, a proximal end of the post 72 and a distal end of the receiving portion or buckle 76 may be longitudinally separated (as seen in FIG. 3, for example) and, accordingly, the medical implant 16 may be in an elongated and generally low-profile "delivery" configuration suitable for percutaneous translation through a patient's anatomy to an area of interest and/or target site.

Figure 4:
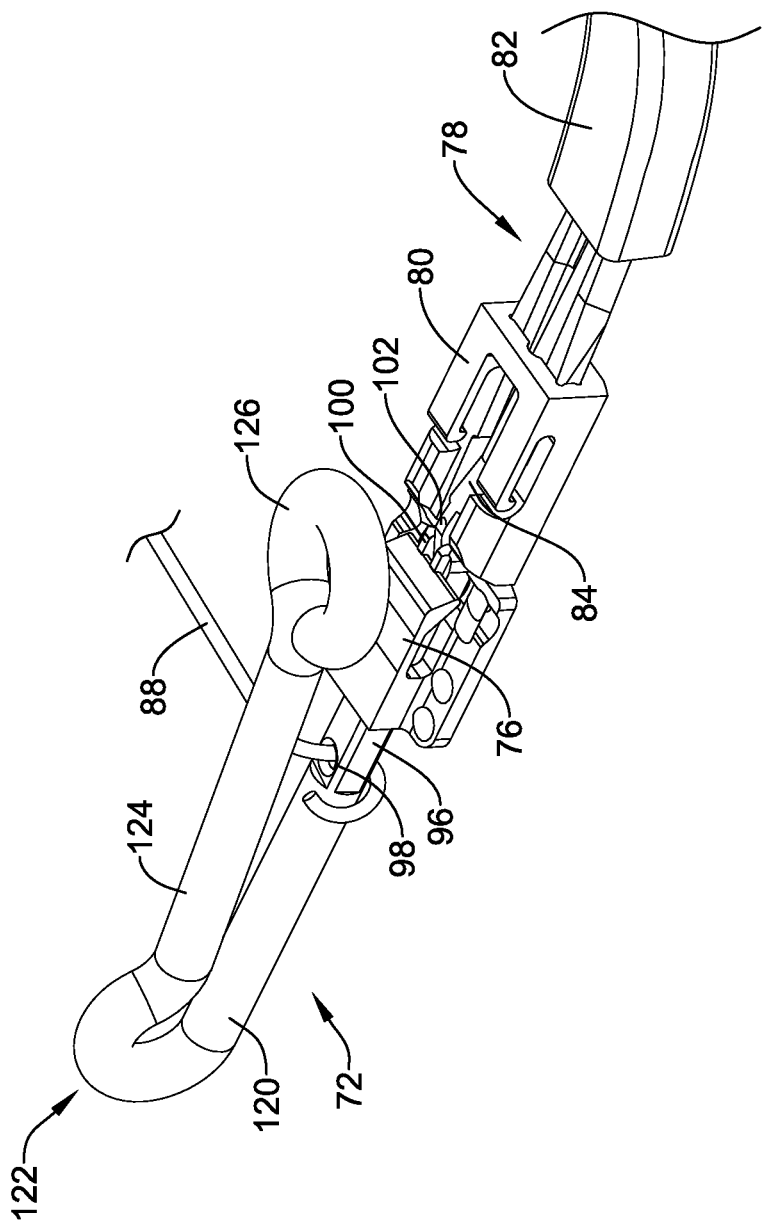
FIG. 4 illustrates selected components of an example implant associated with the example medical device system in a deployed configuration.
Figure 5:
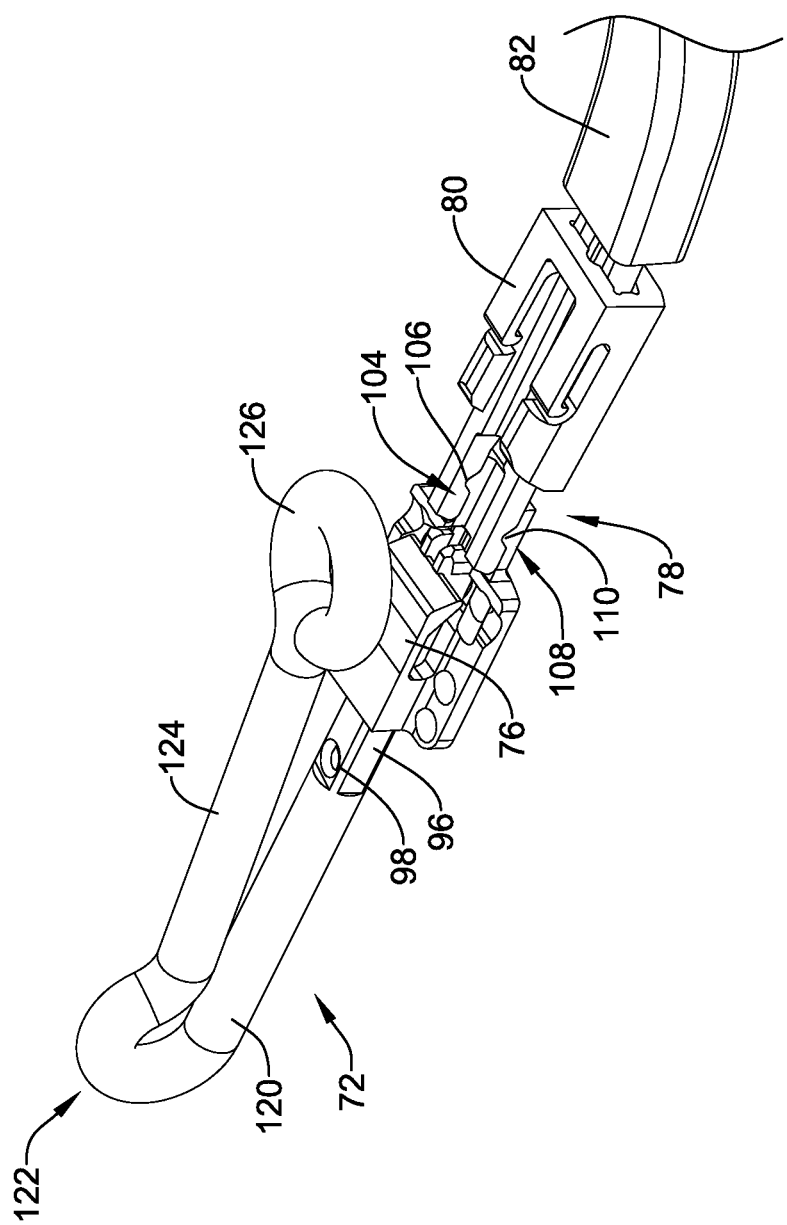
FIG. 5 illustrates selected components of an example implant associated with the example medical device system further translated from the deployed configuration toward a released configuration.

When medical implant 16 reaches the intended target site within the anatomy, a clinician can proximally retract the actuator element or push-pull rod 84 (for example, by using or actuating the handle 18 or a portion thereof), thereby moving a proximal end of the bar portion 96 of the post 72 toward a distal end of the receiving portion or buckle 76 (as seen in FIG. 4, for example) in order to axially shorten and/or radially expand the anchor member or braid 70 of the medical implant 16 towards the "deployed" configuration. When retracting or pulling the actuator element or push-pull rod 84 proximally, the pin 88, positioned through the opening 98 in the post 72, is disposed through a distal end of the elongated aperture or slot. Ultimately, the actuator element or push-pull rod 84 can be retracted sufficiently far enough to lock the post 72 with the receiving portion or buckle 76 so as to lock the medical implant 16 in the "deployed" configuration (as seen in FIGS. 4 and 5, for example), suitable for implantation within the anatomy. In other words, in some embodiments, axial translation of the actuator element or push-pull rod 84 (and therefore the post 72 connected thereto) in a proximal direction relative to the receiving portion or buckle 76 may actuate the anchor member or braid 70 from the "delivery" configuration to the "deployed" configuration.

FIG. 4 illustrates the actuator element or push-pull rod 84 proximally retracted such that the proximal end of the bar portion 96 of the post 72 is pulled into contact with a distal end of the receiving portion or buckle 76. At this point, the bar portion 96 is pulled into the distal end of the receiving portion or buckle 76. In at least some embodiments, the bar portion 96 may be slidably and non-rotatably received within the receiving portion or buckle 76.

In pulling the bar portion 96 into the receiving portion or buckle 76, a raised, generally transversely-oriented shoulder or ridge 100 disposed on the proximal end of the bar portion 96 of the post 72 may be pulled proximally into the receiving portion or buckle 76 until the raised, generally transversely-oriented shoulder or ridge 100 is pulled past the receiving portion or buckle 76. In this configuration, the receiving portion or buckle 76 engage the raised, generally transversely-oriented shoulder or ridge 100 and the post 72 may be secured to the receiving portion or buckle 76, thereby preventing distal movement of the post 72 relative to the receiving portion or buckle 76, such as under rebound stress from the anchor member or braid 70.

However, at this point, it may be possible to urge the actuator element or push-pull rod 84 distally to "unlock" the medical implant 16, thereby allowing for repositioning and/or retraction of the medical implant 16. When the actuator element or push-pull rod 84 is urged distally, the actuator element or push-pull rod 84 may be translated distally relative to the locking mechanism (i.e., the post 72 and/or the receiving portion or buckle 76), so as to position the pin 88 extending through the opening 98 in a proximal end of the elongated aperture or slot. Once the pin 88 is positioned in the proximal end of the elongated aperture or slot, the post 72 may move distally along with the actuator element or push-pull rod 84 relative to the receiving portion or buckle 76.

A longitudinally-oriented ridge 102 on the distal portion of the actuator element or push-pull rod 84, either alone or as a part of the keyed orienting structure, may include a distally inclined surface configured to engage the receiving portion or buckle 76 when the actuator element or push-pull rod 84 is advanced distally. As such, the receiving portion or buckle 76 may ride up the inclined surface of the longitudinally-oriented ridge 102, thereby allowing generally transversely-oriented ridge 100 on the bar portion 96 of the post 72 to disengage from the receiving portion or buckle 76 and translate distally therethrough. In other words, distal axial translation of the actuator element or push-pull rod 84 unlocks the anchor member or braid 70 from the "deployed" configuration.

With the pin 88 positioned at the proximal end of the elongate aperture or slot, further distal urging of the actuator element or push-pull rod 84 will no longer cause translation of the actuator element or push-pull rod 84 relative to the locking mechanism as a whole. Instead, further distal urging (i.e., distal axial translation) of the actuator element or push-pull rod 84 will result in the actuator element or push-pull rod 84 and the post 72, joined together by the pin 88, to translate distally relative to the receiving portion or buckle 76, thereby actuating the anchor member or braid 70 from the "deployed" configuration toward the "delivery" configuration.

Alternatively, if a clinician is satisfied with the positioning and/or locking of the medical implant 16 (e.g., after visualization of the medical implant 16 via a suitable imaging technique), the pin 88 may be pulled (e.g., removed from opening 98 and the elongated aperture or slot at the distal end of the actuator element or push-pull rod 84) to uncouple and/or disengage the actuator element or push-pull rod 84 from the post 72, thereby permitting proximal retraction of the actuator element or push-pull rod 84 from the post 72, as seen in FIG. 5, for example.

Figure 6:
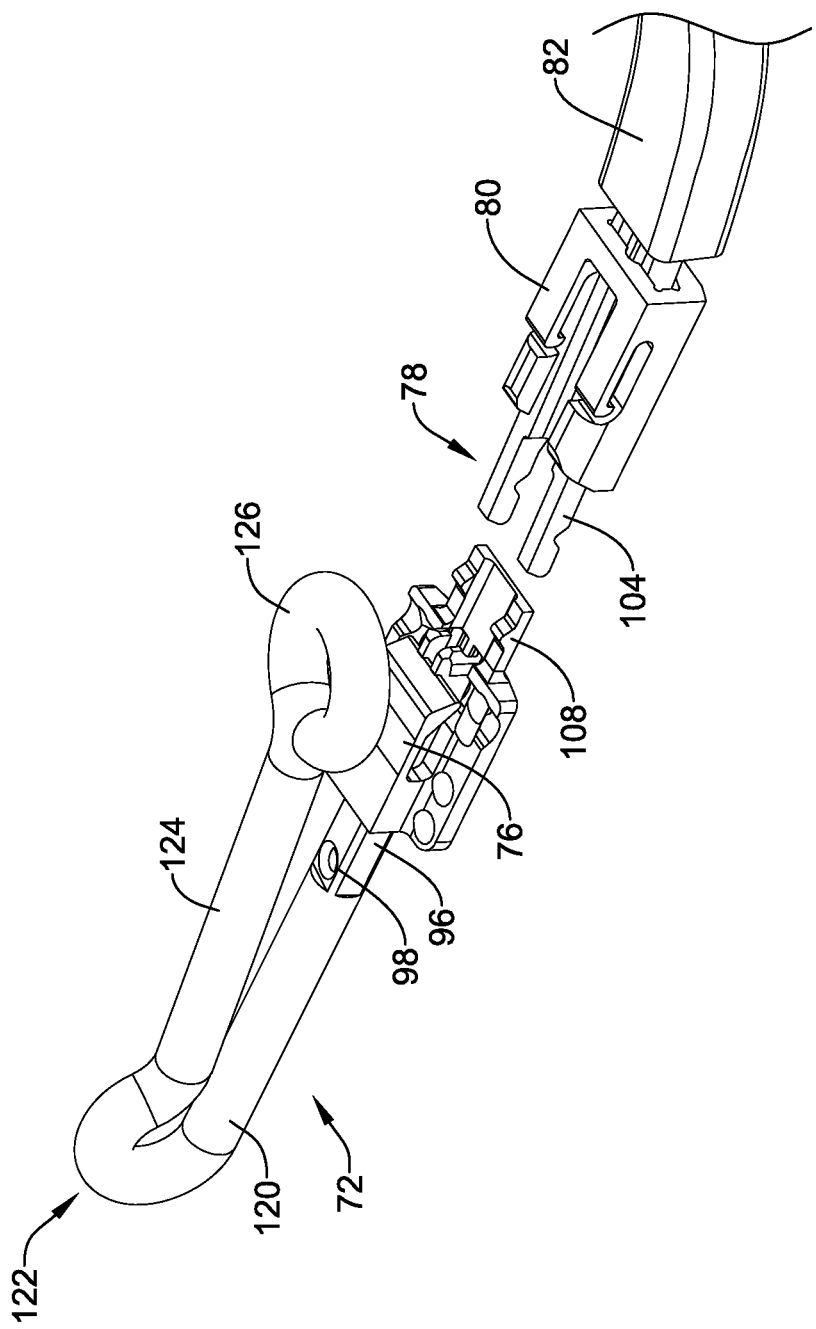
FIG. 6 illustrates selected components of an example implant associated with the example medical device system further translated from the deployed configuration toward a released configuration.

Further retraction of the actuator element or push-pull rod 84 may cause the longitudinally-oriented ridge 102 on the distal portion of the actuator element or push-pull rod 84 to engage the collar 80 and cause the collar 80 to slide proximally along the finger of the coupler 78 as the actuator element or push-pull rod 84 is retracted proximally. In doing so, a forked end 104, which has a groove 106 formed therein, of the finger of the coupler 78, is exposed and can be uncoupled from a rail 108, which has a projection 110 formed thereon that is configured to matingly engage with the groove 106, on the proximal end of the receiving portion or buckle 76, as shown in FIG. 5. After the forked end 104 has disengaged from the rail 108, further proximal retraction of the at least one actuator element or push-pull rod 84 causes the finger of the coupler 78 to retract proximally from the locking mechanism and the medical implant 16, as seen in FIG. 6, for example, thereby leaving the medical implant 16 disposed at the target site in the "released" configuration.

Figure 7:
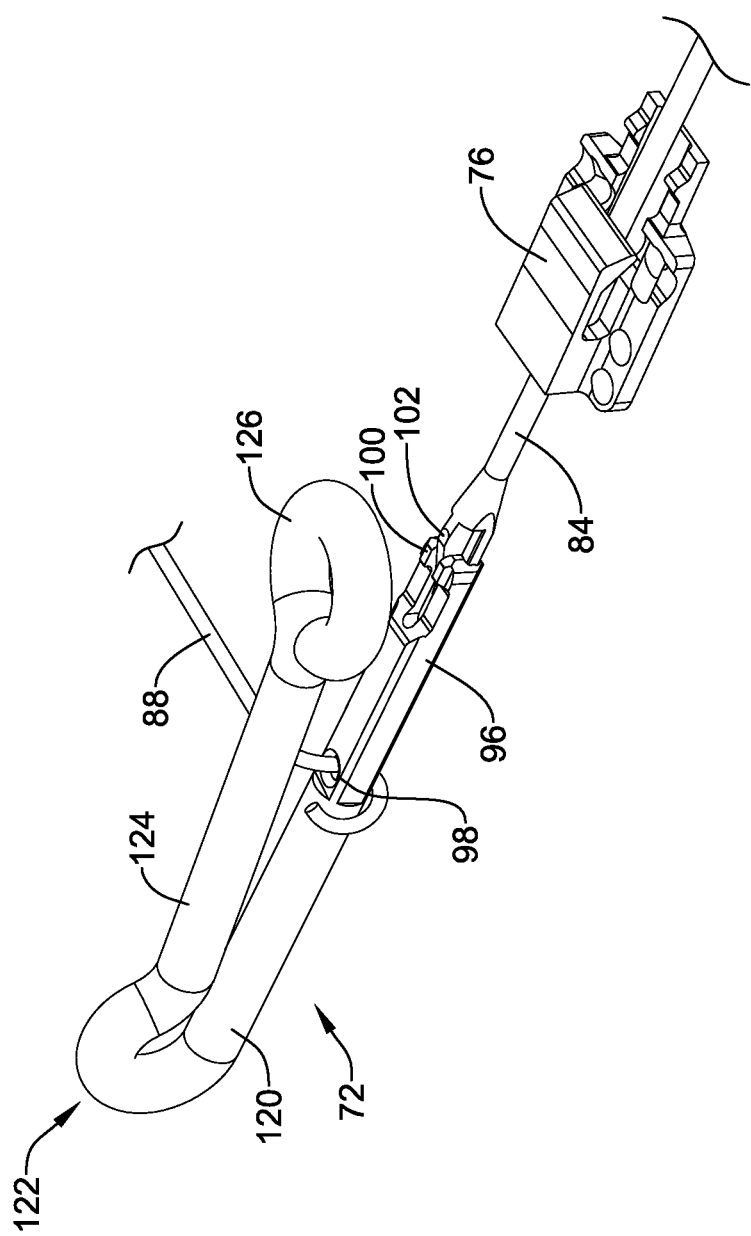
FIG. 7 illustrates selected components of an example implant associated with the example medical device system in a delivery configuration.
Figure 8:
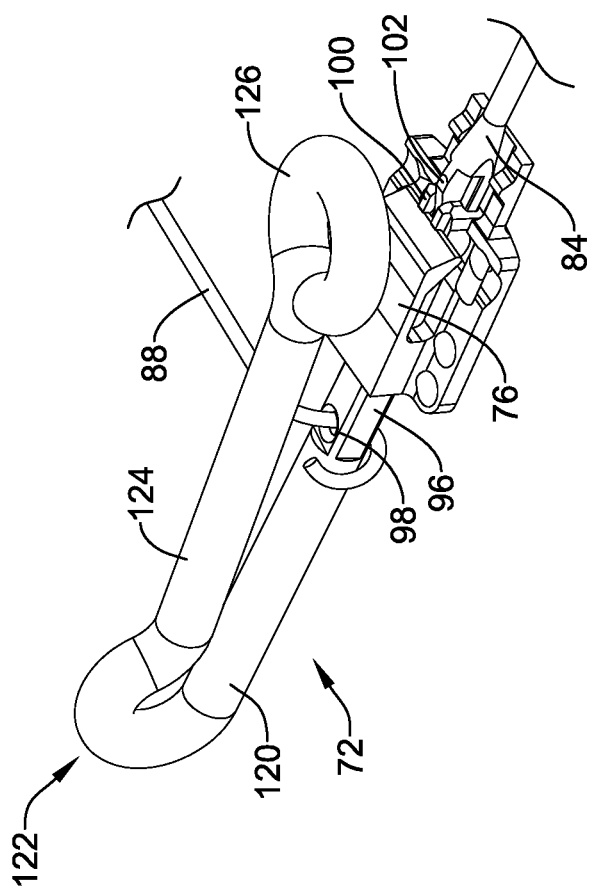
FIG. 8 illustrates selected components of an example implant associated with the example medical device system in a deployed configuration.

FIGS. 7 and 8 illustrate selected components associated with a medical implant 16 of a medical device system 10 as described above, when the medical implant is in the "delivery" configuration and the "deployed" configuration, respectively. As may be seen in FIG. 7, and similar to the discussion above, a locking mechanism may include an axially movable post 72 and a receiving portion or buckle 76. An element of a delivery device, such as an actuator element or push-pull rod 84 may be translatably disposed through the receiving portion or buckle 76 and releasably engaged with and/or attached to the post 72. In some embodiments, a distal portion of the actuator element or push-pull rod 84 may include a keyed orienting feature configured to slidably and/or matingly engage a corresponding passage extending into a proximal end of a bar portion 96 of the post 72. In at least some embodiments, the keyed orienting feature and/or the passage extending into the proximal end of the bar portion 96 may prevent relative rotation between the actuator element or push-pull rod 84 and the post 72.

In some embodiments, a distal portion of the keyed orienting feature may be substantially flattened into a generally transversely-oriented cross-section extending along a majority of the keyed orienting feature. A distal portion of the passage extending into the proximal end of the bar portion 96 may be slot-shaped to correspond to and slidingly accept the flattened, generally transversely-oriented cross-section of the keyed orienting feature therein. In some embodiments, a proximal portion of the keyed orienting feature may be substantially T-shaped and/or may include a longitudinally-oriented ridge 102 arranged generally orthogonally to the flattened, generally transversely-oriented cross-section of the distal portion of the keyed orienting feature. A proximal portion of the passage extending into the bar portion 96 may include a corresponding T-shape configured to slidingly accept the keyed orienting feature of the actuator element of push-pull rod 84 therein.

Adjacent a distal end of the passage extending into the bar portion 96, an opening 98 may pass through the bar portion 96 generally perpendicular to the distal portion of the keyed orienting feature, such that the opening 98 aligns with the elongated aperture or slot at the distal end of the actuator element or push-pull rod 84. A pin 88 may extend through the opening 98 and the elongated aperture or slot at the distal end of the actuator element or push-pull rod 84 to couple the actuator element or push-pull rod 84 to the post 72.

In at least some embodiments, the post 72 may include a distally-extending body portion 120, the body portion 120 extending distally from the bar portion 96 toward a distal end of the anchor member or braid 70. In some embodiments, the body portion 120 may be unitary with and/or integrally formed with the bar portion 96 as and/or from a single piece of material. In some embodiments, the body portion 120 and the bar portion 96 may be formed from a single piece of wire, round stock, or other suitable material. In some embodiments, the bar portion 96 may be generally polygonal (i.e., two-sided, three-sided, four-sided, five-sided, six-sided, etc.) in shape. Other shapes, both regular and irregular, are also contemplated. In some embodiments, the bar portion 96 may be formed by further processing the single piece of wire, round stock, or other suitable material, such as by machining, stamping, laser cutting, etc. In some embodiments, the bar portion 96 may be prevented from rotating (i.e., is non-rotatable) relative to the receiving portion or buckle 76 when the bar portion 96 is engaged with the receiving portion or buckle 76.

In some embodiments, a distal end of the post 72 may include a flexible hinge portion 122. In some embodiments, the hinge portion 122 connects the body portion 120 to a leg portion 124 extending radially inwardly (with respect to the anchor member or braid 70) from the body portion 120 of the post 72. In some embodiments, the leg portion 124 may be cantilevered from the hinge portion 122 and/or the body portion 120. In some embodiments, the hinge portion 122 may be an extension of the body portion 120 that bends at least partially back upon itself and transitions into the leg portion 124. In some embodiments, the hinge portion 122 may have and/or include a radius of curvature. For example, in some embodiments, the radius of curvature may be between 0 and 3 millimeters (mm). In some embodiments, the hinge portion 122 may be configured to dispose the body portion 120 and the leg portion 124 at an acute angle relative to each other. In some embodiments, the acute angle may be between about 0 degrees and about 90 degrees, between about 3 degrees and about 60 degrees, between about 5 degrees and about 45 degrees, between about 8 degrees and about 30 degrees, between about 10 degrees and about 20 degrees, between about 12 degrees and about 16 degrees, about 14 degrees, or another suitable angle. In at least some embodiments, the hinge portion 122 flexibly attaches the leg portion 124 to the body portion 120 of the post 72. In some embodiments, the leg portion 124 may extend from the body portion 120 of the post 72 toward a proximal end of the anchor member or braid 70. In some embodiments, the leg portion 124 may be attached to the body portion 120 of the post 72 at the distal end of the body portion 120 of the post 72. In some embodiments, at least part of the leg portion 124 may longitudinally overlap the receiving portion or buckle 76 along a central longitudinal axis of the anchor member or braid 70 in the "deployed" configuration.

In some embodiments, the leg portion 124 may include a free end 126 and a secured end, where the leg portion 124 may be attached to the body portion 120 of the post 72 at the secured end, which may connect directly to the hinge portion 122. In some embodiments, the free end 126 of the leg portion 124 may be unattached (i.e., not directly attached) to any other structure of the medical implant 16, except for the leg portion 124 and/or the plurality of valve leaflets 68. In other words, in some embodiments, the free end 126 may not be directly attached to any other structure or feature of the medical implant 16 (i.e., the receiving portion or buckle 76, the anchor member or braid 70, etc.). In some embodiments, a distalmost end of the post 72, which in at least some embodiments may be and/or include the hinge portion 122, may be coupled to the distal end of the anchor member or braid 70, such as, for example, by a coupling member such as a suture, filament, wire, or other suitable means. As such, when the post 72 is pulled proximally to engage the receiving portion or buckle 76, the distal end of the anchor member or braid 70 is also pulled proximally relative to the receiving portion or buckle 76, thereby transitioning from the "delivery" configuration toward the "deployed" configuration.

In at least some embodiments, one or more of the plurality of valve leaflets 68 may be attached to the leg portion 124. In some embodiments, the plurality of valve leaflets 68 may be secured directly to the leg portion 124. In some embodiments, the plurality of valve leaflets 68 may not be directly secured to the body portion 120 and/or the bar portion 96 of the post 72, but is instead coupled to the post 72 via the leg portion 124. In some embodiments, the plurality of valve leaflets 68 may be wrapped around the leg portion 124. In some embodiments, a distalmost end of the plurality of valve leaflets may be coupled to the distal end of the anchor member or braid 70. In some embodiments, the plurality of valve leaflets 68 may be coupled and/or secured (i.e., to the leg portion 124, to the anchor member or braid 70, and/or back to themselves) using one or more sutures, threads, wires, filaments, or other suitable elements. In some embodiments, the plurality of valve leaflets 68 may be coupled and/or secured (i.e., to the leg portion 124, to the anchor member or braid 70, and/or back to themselves) using an adhesive, a bonding agent, or other suitable securing means. In some embodiments, the plurality of valve leaflets 68 may be coupled and/or secured (i.e., to the leg portion 124, to the anchor member or braid 70, and/or back to themselves) using a fabric, a textile, or other thin flexible material.

Figure 9:
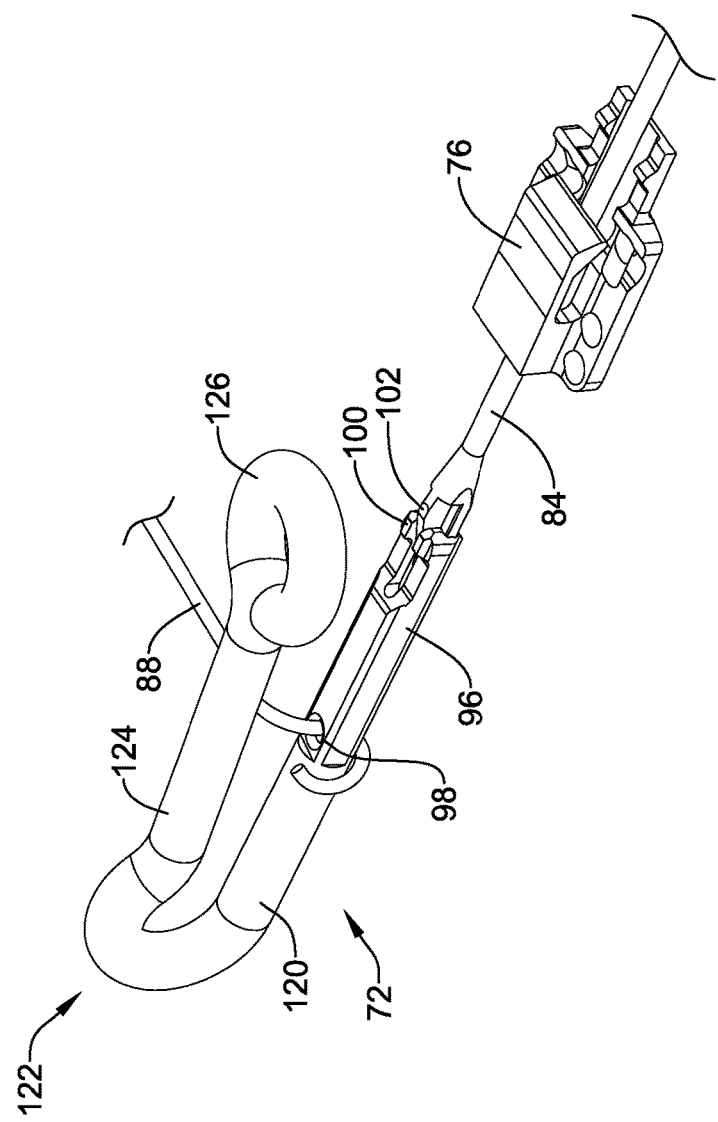
FIG. 9 illustrates selected components of an example implant associated with the example medical device system in a delivery configuration.
Figure 10:
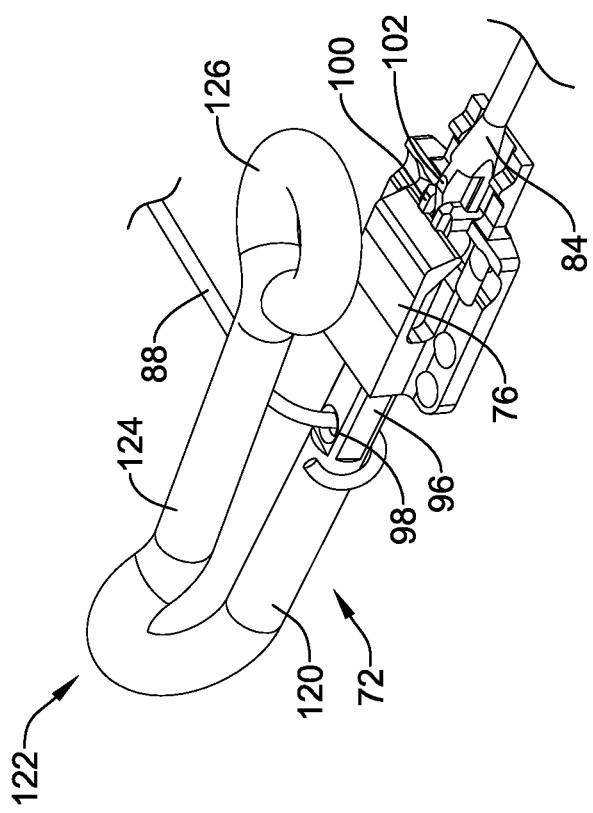
FIG. 10 illustrates selected components of an example implant associated with the example medical device system in a deployed configuration.

FIGS. 9 and 10 illustrate selected components associated with a medical implant 16 of a medical device system 10 as described above, when the medical implant is in the "delivery" configuration and the "deployed" configuration, respectively. As may be seen in FIG. 9, and similar to the discussion above, a locking mechanism may include an axially movable post 72 and a receiving portion or buckle 76. An element of a delivery device, such as an actuator element or push-pull rod 84 may be translatably disposed through the receiving portion or buckle 76 and releasably engaged with and/or attached to the post 72. In some embodiments, a distal portion of the actuator element or push-pull rod 84 may include a keyed orienting feature configured to slidably and/or matingly engage a corresponding passage extending into a proximal end of a bar portion 96 of the post 72. In at least some embodiments, the keyed orienting feature and/or the passage extending into the proximal end of the bar portion 96 may prevent relative rotation between the actuator element or push-pull rod 84 and the post 72.

In some embodiments, a distal portion of the keyed orienting feature may be substantially flattened into a generally transversely-oriented cross-section extending along a majority of the keyed orienting feature. A distal portion of the passage extending into the proximal end of the bar portion 96 may be slot-shaped to correspond to and slidingly accept the flattened, generally transversely-oriented cross-section of the keyed orienting feature therein. In some embodiments, a proximal portion of the keyed orienting feature may be substantially T-shaped and/or may include a longitudinally-oriented ridge 102 arranged generally orthogonally to the flattened, generally transversely-oriented cross-section of the distal portion of the keyed orienting feature. A proximal portion of the passage extending into the bar portion 96 may include a corresponding T-shape configured to slidingly accept the keyed orienting feature of the actuator element of push-pull rod 84 therein.

Adjacent a distal end of the passage extending into the bar portion 96, an opening 98 may pass through the bar portion 96 generally perpendicular to the distal portion of the keyed orienting feature, such that the opening 98 aligns with the elongated aperture or slot at the distal end of the actuator element or push-pull rod 84. A pin 88 may extend through the opening 98 and the elongated aperture or slot at the distal end of the actuator element or push-pull rod 84 to couple the actuator element or push-pull rod 84 to the post 72.

In at least some embodiments, the post 72 may include a distally-extending body portion 120, the body portion 120 extending distally from the bar portion 96 toward a distal end of the anchor member or braid 70. In some embodiments, the body portion 120 may be unitary with and/or integrally formed with the bar portion 96 as and/or from a single piece of material. In some embodiments, the body portion 120 and the bar portion 96 may be formed from a single piece of wire, round stock, or other suitable material. In some embodiments, the bar portion 96 may be generally polygonal (i.e., two-sided, three-sided, four-sided, five-sided, six-sided, etc.) in shape. Other shapes, both regular and irregular, are also contemplated. In some embodiments, the bar portion 96 may be formed by further processing the single piece of wire, round stock, or other suitable material, such as by machining, stamping, laser cutting, etc. In some embodiments, the bar portion 96 may be prevented from rotating (i.e., is non-rotatable) relative to the receiving portion or buckle 76 when the bar portion 96 is engaged with the receiving portion or buckle 76.

In some embodiments, a distal end of the post 72 may include a flexible hinge portion 122. In some embodiments, the hinge portion 122 connects the body portion 120 to a leg portion 124 extending radially inwardly (with respect to the anchor member or braid 70) from the body portion 120 of the post 72. In some embodiments, the leg portion 124 may be cantilevered from the hinge portion 122 and/or the body portion 120. In some embodiments, the hinge portion 122 may be an extension of the body portion 120 that bends at least partially back upon itself and transitions into the leg portion 124. In some embodiments, the hinge portion 122 may have and/or include a radius of curvature. For example, in some embodiments, the radius of curvature may be between 0 and 3 millimeters (mm). In some embodiments, the hinge portion 122 may be configured to dispose the body portion 120 and the leg portion 124 at an acute angle relative to each other. In some embodiments, the acute angle may be between about 0 degrees and about 90 degrees, between about 3 degrees and about 60 degrees, between about 5 degrees and about 45 degrees, between about 8 degrees and about 30 degrees, between about 10 degrees and about 20 degrees, between about 12 degrees and about 16 degrees, about 14 degrees, or another suitable angle. In at least some embodiments, the hinge portion 122 flexibly attaches the leg portion 124 to the body portion 120 of the post 72. In some embodiments, the leg portion 124 may extend from the body portion 120 of the post 72 toward a proximal end of the anchor member or braid 70. In some embodiments, the leg portion 124 may be attached to the body portion 120 of the post 72 at the distal end of the body portion 120 of the post 72. In some embodiments, at least part of the leg portion 124 may longitudinally overlap the receiving portion or buckle 76 along a central longitudinal axis of the anchor member or braid 70 in the "deployed" configuration.

In some embodiments, the leg portion 124 may include a free end 126 and a secured end, where the leg portion 124 may be attached to the body portion 120 of the post 72 at the secured end, which may connect directly to the hinge portion 122. In some embodiments, the free end 126 of the leg portion 124 may be unattached (i.e., not directly attached) to any other structure of the medical implant 16, except for the leg portion 124 and/or the plurality of valve leaflets 68. In other words, in some embodiments, the free end 126 may not be directly attached to any other structure or feature of the medical implant 16 (i.e., the receiving portion or buckle 76, the anchor member or braid 70, etc.). In some embodiments, a distalmost end of the post 72, which in at least some embodiments may be and/or include the hinge portion 122, may be coupled to the distal end of the anchor member or braid 70, such as, for example, by a coupling member such as a suture, filament, wire, or other suitable means. As such, when the post 72 is pulled proximally to engage the receiving portion or buckle 76, the distal end of the anchor member or braid 70 is also pulled proximally relative to the receiving portion or buckle 76, thereby transitioning from the "delivery" configuration toward the "deployed" configuration.

In at least some embodiments, one or more of the plurality of valve leaflets 68 may be attached to the leg portion 124. In some embodiments, the plurality of valve leaflets 68 may be secured directly to the leg portion 124. In some embodiments, the plurality of valve leaflets 68 may not be directly secured to the body portion 120 and/or the bar portion 96 of the post 72, but is instead coupled to the post 72 via the leg portion 124. In some embodiments, the plurality of valve leaflets 68 may be wrapped around the leg portion 124. In some embodiments, a distalmost end of the plurality of valve leaflets may be coupled to the distal end of the anchor member or braid 70. In some embodiments, the plurality of valve leaflets 68 may be coupled and/or secured (i.e., to the leg portion 124, to the anchor member or braid 70, and/or back to themselves) using one or more sutures, threads, wires, filaments, or other suitable elements. In some embodiments, the plurality of valve leaflets 68 may be coupled and/or secured (i.e., to the leg portion 124, to the anchor member or braid 70, and/or back to themselves) using an adhesive, a bonding agent, or other suitable securing means. In some embodiments, the plurality of valve leaflets 68 may be coupled and/or secured (i.e., to the leg portion 124, to the anchor member or braid 70, and/or back to themselves) using a fabric, a textile, or other thin flexible material.

Figure 11:
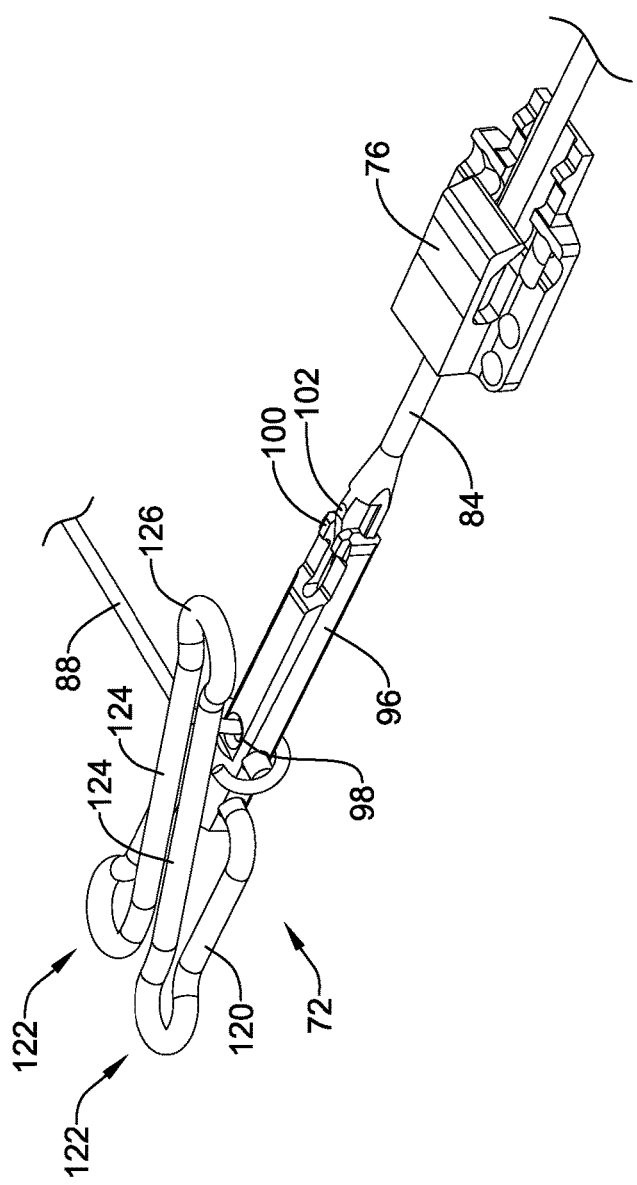
FIG. 11 illustrates selected components of an example implant associated with the example medical device system in a delivery configuration.
Figure 12:
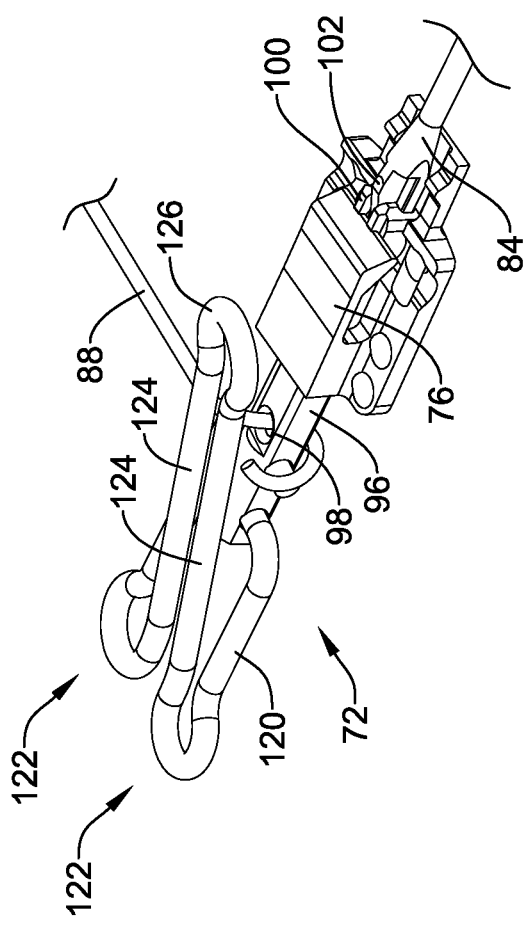
FIG. 12 illustrates selected components of an example implant associated with the example medical device system in a deployed configuration.

FIGS. 11 and 12 illustrate selected components associated with a medical implant 16 of a medical device system 10 as described above, when the medical implant is in the "delivery" configuration and the "deployed" configuration, respectively. As may be seen in FIG. 11, and similar to the discussion above, a locking mechanism may include an axially movable post 72 and a receiving portion or buckle 76. An element of a delivery device, such as an actuator element or push-pull rod 84 may be translatably disposed through the receiving portion or buckle 76 and releasably engaged with and/or attached to the post 72. In some embodiments, a distal portion of the actuator element or push-pull rod 84 may include a keyed orienting feature configured to slidably and/or matingly engage a corresponding passage extending into a proximal end of a bar portion 96 of the post 72. In at least some embodiments, the keyed orienting feature and/or the passage extending into the proximal end of the bar portion 96 may prevent relative rotation between the actuator element or push-pull rod 84 and the post 72.

In some embodiments, a distal portion of the keyed orienting feature may be substantially flattened into a generally transversely-oriented cross-section extending along a majority of the keyed orienting feature. A distal portion of the passage extending into the proximal end of the bar portion 96 may be slot-shaped to correspond to and slidingly accept the flattened, generally transversely-oriented cross-section of the keyed orienting feature therein. In some embodiments, a proximal portion of the keyed orienting feature may be substantially T-shaped and/or may include a longitudinally-oriented ridge 102 arranged generally orthogonally to the flattened, generally transversely-oriented cross-section of the distal portion of the keyed orienting feature. A proximal portion of the passage extending into the bar portion 96 may include a corresponding T-shape configured to slidingly accept the keyed orienting feature of the actuator element of push-pull rod 84 therein.

Adjacent a distal end of the passage extending into the bar portion 96, an opening 98 may pass through the bar portion 96 generally perpendicular to the distal portion of the keyed orienting feature, such that the opening 98 aligns with the elongated aperture or slot at the distal end of the actuator element or push-pull rod 84. A pin 88 may extend through the opening 98 and the elongated aperture or slot at the distal end of the actuator element or push-pull rod 84 to couple the actuator element or push-pull rod 84 to the post 72.

In at least some embodiments, the post 72 may include a distally-extending body portion 120, the body portion 120 extending distally from the bar portion 96 toward a distal end of the anchor member or braid 70. In some embodiments, the post 72 may include a plurality of body portions 120 extending distally from the bar portion 96 toward the distal end of the anchor member or braid 70. In some embodiments, the plurality of body portions 120 may include two body portions 120, three body portions 120, four body portions 120, or other suitable quantities of body portions 120. In some embodiments, the body portion(s) 120 may be unitary with and/or integrally formed with the bar portion 96 as and/or from a single piece of material. In some embodiments, the body portion(s) 120 may be separately formed from and fixedly attached to the bar portion 96. In some embodiments, a plurality of body portions 120 may be formed from a single piece of wire, round stock, or other suitable material. In some embodiments, the bar portion 96 may include one or more holes or apertures configured to receive and/or secure a proximal end of the body portion(s) 120 therein. In some embodiments, the one or more holes or apertures may be oriented generally transversely with respect to the bar portion 96. In some embodiments, the bar portion 96 may be generally polygonal (i.e., two-sided, three-sided, four-sided, five-sided, six-sided, etc.) in shape. Other shapes, both regular and irregular, are also contemplated. In some embodiments, the bar portion 96 may be prevented from rotating (i.e., is non-rotatable) relative to the receiving portion or buckle 76 when the bar portion 96 is engaged with the receiving portion or buckle 76.

In some embodiments, a distal end of the post 72 may include a flexible hinge portion 122. In some embodiments, a distal end of the post 72 may include a plurality of hinge portions 122 corresponding to and/or fixedly attached to the plurality of body portions 120. In some embodiments, the plurality of hinge portions 122 may include two hinge portions 122, three hinge portions 122, four hinge portions 122, or other suitable quantities of hinge portions 122. In some embodiments, the hinge portion(s) 122 connects the body portion(s) 120 to a leg portion 124 or a plurality of leg portions 124 extending radially inwardly (with respect to the anchor member or braid 70) from the body portion(s) 120 of the post 72. In some embodiments, the leg portion(s) 124 may be cantilevered from the hinge portion(s) 122 and/or the body portion(s) 120. In some embodiments, the plurality of leg portions 124 may include two leg portions 124, three leg portions 124, four leg portions 124, or other suitable quantities of leg portions 124. In some embodiments, the hinge portion(s) 122 may be an extension of the body portion(s) 120 that bends at least partially back upon itself and transitions into the leg portion(s) 124. In some embodiments, the hinge portion(s) 122 may have and/or include a radius of curvature. For example, in some embodiments, the radius of curvature may be between 0 and 3 millimeters (mm). In some embodiments, the hinge portion(s) 122 may be configured to dispose the body portion(s) 120 and the leg portion(s) 124 at an acute angle relative to each other. In some embodiments, the acute angle may be between about 0 degrees and about 90 degrees, between about 3 degrees and about 60 degrees, between about 5 degrees and about 45 degrees, between about 8 degrees and about 30 degrees, between about 10 degrees and about 20 degrees, between about 12 degrees and about 16 degrees, about 14 degrees, or another suitable angle. In at least some embodiments, the hinge portion(s) 122 flexibly attaches the leg portion(s) 124 to the body portion(s) 120 of the post 72. In some embodiments, the leg portion(s) 124 may extend from the body portion(s) 120 of the post 72 toward a proximal end of the anchor member or braid 70. In some embodiments, the leg portion(s) 124 may be attached to the body portion(s) 120 of the post 72 at the distal end of the body portion(s) 120 of the post 72. In some embodiments, at least part of the leg portion(s) 124 may longitudinally overlap the receiving portion or buckle 76 along a central longitudinal axis of the anchor member or braid 70 in the "deployed" configuration.

In some embodiments, the leg portion(s) 124 may include a free end 126 and a secured end, where the leg portion(s) 124 may be attached to the body portion(s) 120 of the post 72 at the secured end, which may connect directly to the hinge portion(s) 122. In some embodiments, the plurality of leg portions 124 may be joined together at the free end 126. In some embodiments, the plurality of leg portions 124 may be arranged generally parallel to each other. In some embodiments, the free end 126 of the leg portion(s) 124 may be unattached (i.e., not directly attached) to any other structure of the medical implant 16, except for the leg portion(s) 124 and/or the plurality of valve leaflets 68. In other words, in some embodiments, the free end 126 may not be directly attached to any other structure or feature of the medical implant 16 (i.e., the receiving portion or buckle 76, the anchor member or braid 70, etc.). In some embodiments, a distalmost end of the post 72, which in at least some embodiments may be and/or include the hinge portion(s) 122, may be coupled to the distal end of the anchor member or braid 70, such as, for example, by a coupling member such as a suture, filament, wire, or other suitable means. As such, when the post 72 is pulled proximally to engage the receiving portion or buckle 76, the distal end of the anchor member or braid 70 is also pulled proximally relative to the receiving portion or buckle 76, thereby transitioning from the "delivery" configuration toward the "deployed" configuration.

In at least some embodiments, one or more of the plurality of valve leaflets 68 may be attached to the leg portion(s) 124. In some embodiments at least some of the plurality of valve leaflets 68 may extend and/or pass between the plurality of leg portions 124. In some embodiments, at least some of the plurality of valve leaflets 68 may extend and/or pass between two adjacent leg portions 124. In some embodiments, the plurality of valve leaflets 68 may be secured directly to the leg portion(s) 124. In some embodiments, the plurality of valve leaflets 68 may not be directly secured to the body portion(s) 120 and/or the bar portion 96 of the post 72, but is instead coupled to the post 72 via the leg portion(s) 124. In some embodiments, the plurality of valve leaflets 68 may be wrapped around the leg portion(s) 124. In some embodiments, the at least some of the plurality of valve leaflets 68 extending and/or passing between two adjacent leg portions 124 may wrap around the two adjacent leg portions 124. In some embodiments, a distalmost end of the plurality of valve leaflets 68 may be coupled to the distal end of the anchor member or braid 70. In some embodiments, the plurality of valve leaflets 68 may be coupled and/or secured (i.e., to the leg portion(s) 124, to the anchor member or braid 70, and/or back to themselves) using one or more sutures, threads, wires, filaments, or other suitable elements. In some embodiments, the plurality of valve leaflets 68 may be coupled and/or secured (i.e., to the leg portion(s) 124, to the anchor member or braid 70, and/or back to themselves) using an adhesive, a bonding agent, or other suitable securing means. In some embodiments, the plurality of valve leaflets 68 may be coupled and/or secured (i.e., to the leg portion 124, to the anchor member or braid 70, and/or back to themselves) using a fabric, a textile, or other thin flexible material.

Figure 13:
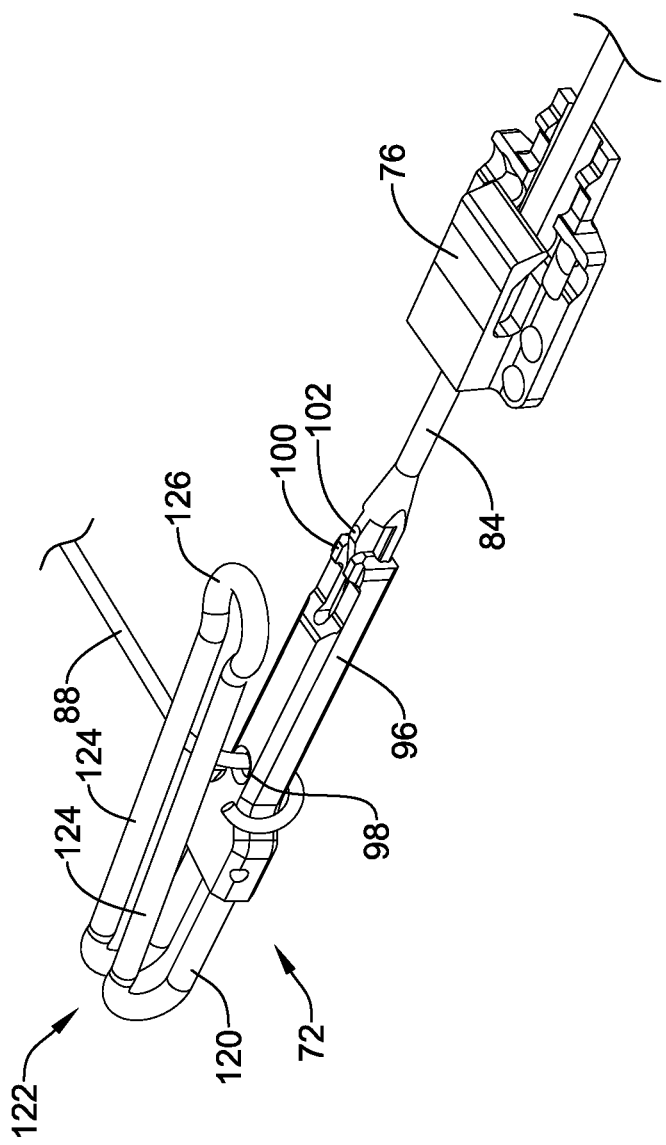
FIG. 13 illustrates selected components of an example implant associated with the example medical device system in a delivery configuration.
Figure 14:
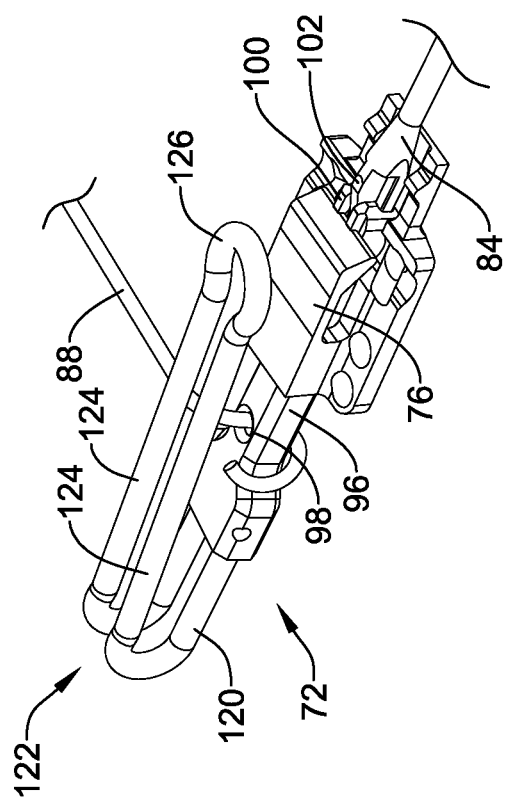
FIG. 14 illustrates selected components of an example implant associated with the example medical device system in a deployed configuration.

FIGS. 13 and 14 illustrate selected components associated with a medical implant 16 of a medical device system 10 as described above, when the medical implant is in the "delivery" configuration and the "deployed" configuration, respectively. As may be seen in FIG. 13, and similar to the discussion above, a locking mechanism may include an axially movable post 72 and a receiving portion or buckle 76. An element of a delivery device, such as an actuator element or push-pull rod 84 may be translatably disposed through the receiving portion or buckle 76 and releasably engaged with and/or attached to the post 72. In some embodiments, a distal portion of the actuator element or push-pull rod 84 may include a keyed orienting feature configured to slidably and/or matingly engage a corresponding passage extending into a proximal end of a bar portion 96 of the post 72. In at least some embodiments, the keyed orienting feature and/or the passage extending into the proximal end of the bar portion 96 may prevent relative rotation between the actuator element or push-pull rod 84 and the post 72.

In some embodiments, a distal portion of the keyed orienting feature may be substantially flattened into a generally transversely-oriented cross-section extending along a majority of the keyed orienting feature. A distal portion of the passage extending into the proximal end of the bar portion 96 may be slot-shaped to correspond to and slidingly accept the flattened, generally transversely-oriented cross-section of the keyed orienting feature therein. In some embodiments, a proximal portion of the keyed orienting feature may be substantially T-shaped and/or may include a longitudinally-oriented ridge 102 arranged generally orthogonally to the flattened, generally transversely-oriented cross-section of the distal portion of the keyed orienting feature. A proximal portion of the passage extending into the bar portion 96 may include a corresponding T-shape configured to slidingly accept the keyed orienting feature of the actuator element of push-pull rod 84 therein.

Adjacent a distal end of the passage extending into the bar portion 96, an opening 98 may pass through the bar portion 96 generally perpendicular to the distal portion of the keyed orienting feature, such that the opening 98 aligns with the elongated aperture or slot at the distal end of the actuator element or push-pull rod 84. A pin 88 may extend through the opening 98 and the elongated aperture or slot at the distal end of the actuator element or push-pull rod 84 to couple the actuator element or push-pull rod 84 to the post 72.

In at least some embodiments, the post 72 may include a distally-extending body portion 120, the body portion 120 extending distally from the bar portion 96 toward a distal end of the anchor member or braid 70. In some embodiments, the post 72 may include a plurality of body portions 120 extending distally from the bar portion 96 toward the distal end of the anchor member or braid 70. In some embodiments, the plurality of body portions 120 may include two body portions 120, three body portions 120, four body portions 120, or other suitable quantities of body portions 120. In some embodiments, the body portion(s) 120 may be unitary with and/or integrally formed with the bar portion 96 as and/or from a single piece of material. In some embodiments, the body portion(s) 120 may be separately formed from and fixedly attached to the bar portion 96. In some embodiments, a plurality of body portions 120 may be formed from a single piece of wire, round stock, or other suitable material. In some embodiments, the bar portion 96 may include one or more holes or apertures configured to receive and/or secure a proximal end of the body portion(s) 120 therein. In some embodiments, the one or more holes or apertures may be oriented generally longitudinally with respect to the bar portion 96. In some embodiments, a transversely-oriented passageway may extend through the bar portion 96 and intersect with the one or more holes or apertures. In some embodiments, a pin may be disposed within the transversely-oriented passageway and engage with a recess or notch in the proximal end of the body portion(s) 120 received within the one or more holes or apertures, thereby securing the body portion(s) 120 to the bar portion 96. In some embodiments, the bar portion 96 may be generally polygonal (i.e., two-sided, three-sided, four-sided, five-sided, six-sided, etc.) in shape. Other shapes, both regular and irregular, are also contemplated. In some embodiments, the bar portion 96 may be prevented from rotating (i.e., is non-rotatable) relative to the receiving portion or buckle 76 when the bar portion 96 is engaged with the receiving portion or buckle 76.

In some embodiments, a distal end of the post 72 may include a flexible hinge portion 122. In some embodiments, a distal end of the post 72 may include a plurality of hinge portions 122 corresponding to and/or fixedly attached to the plurality of body portions 120. In some embodiments, the plurality of hinge portions 122 may include two hinge portions 122, three hinge portions 122, four hinge portions 122, or other suitable quantities of hinge portions 122. In some embodiments, the hinge portion(s) 122 connects the body portion(s) 120 to a leg portion 124 or a plurality of leg portions 124 extending radially inwardly (with respect to the anchor member or braid 70) from the body portion(s) 120 of the post 72. In some embodiments, the leg portion(s) 124 may be cantilevered from the hinge portion(s) 122 and/or the body portion(s) 120. In some embodiments, the plurality of leg portions 124 may include two leg portions 124, three leg portions 124, four leg portions 124, or other suitable quantities of leg portions 124. In some embodiments, the hinge portion(s) 122 may be an extension of the body portion(s) 120 that bends at least partially back upon itself and transitions into the leg portion(s) 124. In some embodiments, the hinge portion(s) 122 may have and/or include a radius of curvature. For example, in some embodiments, the radius of curvature may be between 0 and 3 millimeters (mm). In some embodiments, the hinge portion(s) 122 may be configured to dispose the body portion(s) 120 and the leg portion(s) 124 at an acute angle relative to each other. In some embodiments, the acute angle may be between about 0 degrees and about 90 degrees, between about 3 degrees and about 60 degrees, between about 5 degrees and about 45 degrees, between about 8 degrees and about 30 degrees, between about 10 degrees and about 20 degrees, between about 12 degrees and about 16 degrees, about 14 degrees, or another suitable angle. In at least some embodiments, the hinge portion(s) 122 flexibly attaches the leg portion(s) 124 to the body portion(s) 120 of the post 72. In some embodiments, the leg portion(s) 124 may extend from the body portion(s) 120 of the post 72 toward a proximal end of the anchor member or braid 70. In some embodiments, the leg portion(s) 124 may be attached to the body portion(s) 120 of the post 72 at the distal end of the body portion(s) 120 of the post 72. In some embodiments, at least part of the leg portion(s) 124 may longitudinally overlap the receiving portion or buckle 76 along a central longitudinal axis of the anchor member or braid 70 in the "deployed" configuration.

In some embodiments, the leg portion(s) 124 may include a free end 126 and a secured end, where the leg portion(s) 124 may be attached to the body portion(s) 120 of the post 72 at the secured end, which may connect directly to the hinge portion(s) 122. In some embodiments, the plurality of leg portions 124 may be joined together at the free end 126. In some embodiments, the plurality of leg portions 124 may be arranged generally parallel to each other. In some embodiments, the free end 126 of the leg portion(s) 124 may be unattached (i.e., not directly attached) to any other structure of the medical implant 16, except for the leg portion 124 and/or the plurality of valve leaflets 68. In other words, in some embodiments, the free end 126 may not be directly attached to any other structure or feature of the medical implant 16 (i.e., the receiving portion or buckle 76, the anchor member or braid 70, etc.). In some embodiments, a distalmost end of the post 72, which in at least some embodiments may be and/or include the hinge portion(s) 122, may be coupled to the distal end of the anchor member or braid 70, such as, for example, by a coupling member such as a suture, filament, wire, or other suitable means. As such, when the post 72 is pulled proximally to engage the receiving portion or buckle 76, the distal end of the anchor member or braid 70 is also pulled proximally relative to the receiving portion or buckle 76, thereby transitioning from the "delivery" configuration toward the "deployed" configuration.

In at least some embodiments, one or more of the plurality of valve leaflets 68 may be attached to the leg portion(s) 124. In some embodiments at least some of the plurality of valve leaflets 68 may extend and/or pass between the plurality of leg portions 124. In some embodiments, at least some of the plurality of valve leaflets 68 may extend and/or pass between two adjacent leg portions 124. In some embodiments, the plurality of valve leaflets 68 may be secured directly to the leg portion(s) 124. In some embodiments, the plurality of valve leaflets 68 may not be directly secured to the body portion(s) 120 and/or the bar portion 96 of the post 72, but is instead coupled to the post 72 via the leg portion(s) 124. In some embodiments, the plurality of valve leaflets 68 may be wrapped around the leg portion(s) 124. In some embodiments, the at least some of the plurality of valve leaflets 68 extending and/or passing between two adjacent leg portions 124 may wrap around the two adjacent leg portions 124. In some embodiments, a distalmost end of the plurality of valve leaflets 68 may be coupled to the distal end of the anchor member or braid 70. In some embodiments, the plurality of valve leaflets 68 may be coupled and/or secured (i.e., to the leg portion(s) 124, to the anchor member or braid 70, and/or back to themselves) using one or more sutures, threads, wires, filaments, or other suitable elements. In some embodiments, the plurality of valve leaflets 68 may be coupled and/or secured (i.e., to the leg portion(s) 124, to the anchor member or braid 70, and/or back to themselves) using an adhesive, a bonding agent, or other suitable securing means. In some embodiments, the plurality of valve leaflets 68 may be coupled and/or secured (i.e., to the leg portion 124, to the anchor member or braid 70, and/or back to themselves) using a fabric, a textile, or other thin flexible material.

Figure 15:
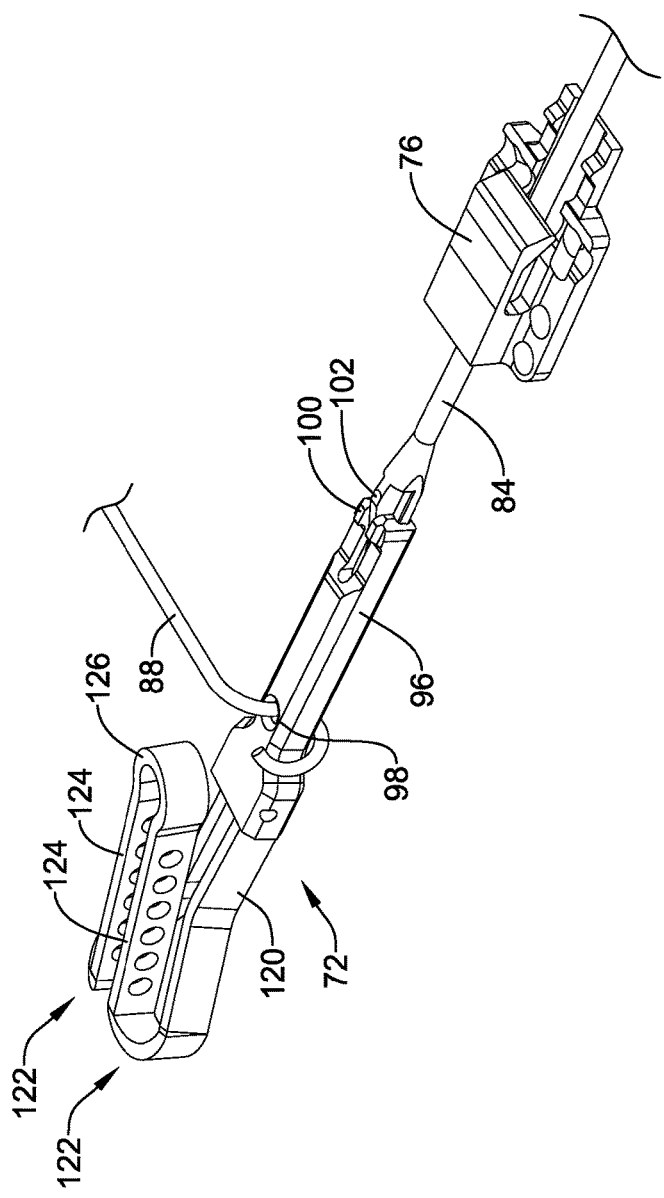
FIG. 15 illustrates selected components of an example implant associated with the example medical device system in a delivery configuration.
Figure 16:
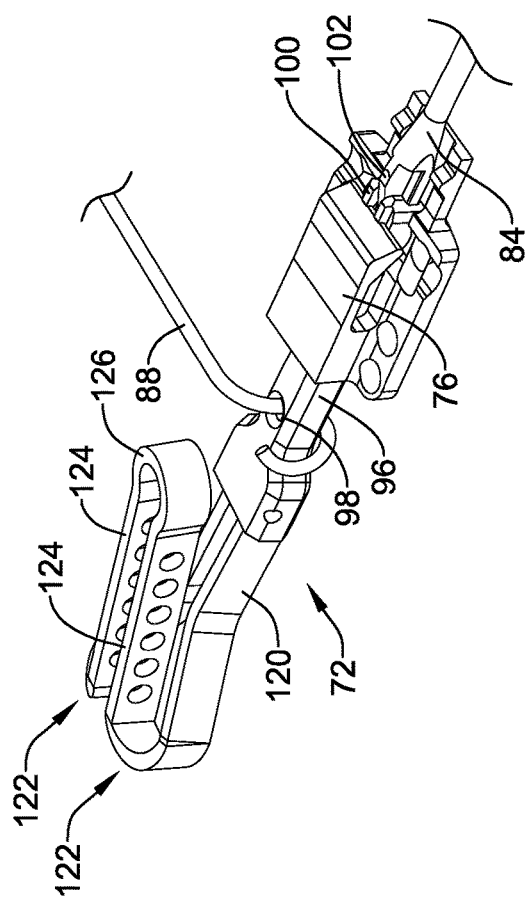
FIG. 16 illustrates selected components of an example implant associated with the example medical device system in a deployed configuration.

FIGS. 15 and 16 illustrate selected components associated with a medical implant 16 of a medical device system 10 as described above, when the medical implant is in the "delivery" configuration and the "deployed" configuration, respectively. As may be seen in FIG. 15, and similar to the discussion above, a locking mechanism may include an axially movable post 72 and a receiving portion or buckle 76. An element of a delivery device, such as an actuator element or push-pull rod 84 may be translatably disposed through the receiving portion or buckle 76 and releasably engaged with and/or attached to the post 72. In some embodiments, a distal portion of the actuator element or push-pull rod 84 may include a keyed orienting feature configured to slidably and/or matingly engage a corresponding passage extending into a proximal end of a bar portion 96 of the post 72. In at least some embodiments, the keyed orienting feature and/or the passage extending into the proximal end of the bar portion 96 may prevent relative rotation between the actuator element or push-pull rod 84 and the post 72.

In some embodiments, a distal portion of the keyed orienting feature may be substantially flattened into a generally transversely-oriented cross-section extending along a majority of the keyed orienting feature. A distal portion of the passage extending into the proximal end of the bar portion 96 may be slot-shaped to correspond to and slidingly accept the flattened, generally transversely-oriented cross-section of the keyed orienting feature therein. In some embodiments, a proximal portion of the keyed orienting feature may be substantially T-shaped and/or may include a longitudinally-oriented ridge 102 arranged generally orthogonally to the flattened, generally transversely-oriented cross-section of the distal portion of the keyed orienting feature. A proximal portion of the passage extending into the bar portion 96 may include a corresponding T-shape configured to slidingly accept the keyed orienting feature of the actuator element of push-pull rod 84 therein.

Adjacent a distal end of the passage extending into the bar portion 96, an opening 98 may pass through the bar portion 96 generally perpendicular to the distal portion of the keyed orienting feature, such that the opening 98 aligns with the elongated aperture or slot at the distal end of the actuator element or push-pull rod 84. A pin 88 may extend through the opening 98 and the elongated aperture or slot at the distal end of the actuator element or push-pull rod 84 to couple the actuator element or push-pull rod 84 to the post 72.

In at least some embodiments, the post 72 may include a distally-extending body portion 120, the body portion 120 extending distally from the bar portion 96 toward a distal end of the anchor member or braid 70. In some embodiments, the post 72 may include a plurality of body portions 120 extending distally from the bar portion 96 toward the distal end of the anchor member or braid 70. In some embodiments, the plurality of body portions 120 may include two body portions 120, three body portions 120, four body portions 120, or other suitable quantities of body portions 120. In some embodiments, the body portion(s) 120 may be unitary with and/or integrally formed with the bar portion 96 as and/or from a single piece of material. In some embodiments, the body portion(s) 120 may be separately formed from and fixedly attached to the bar portion 96. In some embodiments, a plurality of body portions 120 may be formed from a single piece of sheet material, flat stock, or other suitable material by laser cutting, machining, punching, or stamping, for example, and then formed into the desired configuration, such as by bending, stamping, etc. In some embodiments, the bar portion 96 may include one or more holes or apertures configured to receive and/or secure a proximal end of the body portion(s) 120 therein. In some embodiments, the one or more holes or apertures may be oriented generally longitudinally with respect to the bar portion 96. In some embodiments, a transversely-oriented passageway may extend through the bar portion 96 and intersect with the one or more holes or apertures. In some embodiments, a pin may be disposed within the transversely-oriented passageway and engage with a recess, a notch, or a hole in the proximal end of the body portion(s) 120 received within the one or more holes or apertures, thereby securing the body portion(s) 120 to the bar portion 96. In some embodiments, the bar portion 96 may be generally polygonal (i.e., two-sided, three-sided, four-sided, five-sided, six-sided, etc.) in shape. Other shapes, both regular and irregular, are also contemplated. In some embodiments, the bar portion 96 may be prevented from rotating (i.e., is non-rotatable) relative to the receiving portion or buckle 76 when the bar portion 96 is engaged with the receiving portion or buckle 76.

In some embodiments, a distal end of the post 72 may include a flexible hinge portion 122. In some embodiments, a distal end of the post 72 may include a plurality of hinge portions 122 corresponding to and/or fixedly attached to the plurality of body portions 120. In some embodiments, the plurality of hinge portions 122 may include two hinge portions 122, three hinge portions 122, four hinge portions 122, or other suitable quantities of hinge portions 122. In some embodiments, the hinge portion(s) 122 connects the body portion(s) 120 to a leg portion 124 or a plurality of leg portions 124 extending radially inwardly (with respect to the anchor member or braid 70) from the body portion(s) 120 of the post 72. In some embodiments, the leg portion(s) 124 may be cantilevered from the hinge portion(s) 122 and/or the body portion(s) 120. In some embodiments, the plurality of leg portions 124 may include two leg portions 124, three leg portions 124, four leg portions 124, or other suitable quantities of leg portions 124. In some embodiments, the hinge portion(s) 122 may be an extension of the body portion(s) 120 that bends at least partially back upon itself and transitions into the leg portion(s) 124. In some embodiments, the hinge portion(s) 122 may have and/or include a radius of curvature. For example, in some embodiments, the radius of curvature may be between 0 and 3 millimeters (mm). In some embodiments, the hinge portion(s) 122 may be configured to dispose the body portion(s) 120 and the leg portion(s) 124 at an acute angle relative to each other. In some embodiments, the acute angle may be between about 0 degrees and about 90 degrees, between about 3 degrees and about 60 degrees, between about 5 degrees and about 45 degrees, between about 8 degrees and about 30 degrees, between about 10 degrees and about 20 degrees, between about 12 degrees and about 16 degrees, about 14 degrees, or another suitable angle. In at least some embodiments, the hinge portion(s) 122 flexibly attaches the leg portion(s) 124 to the body portion(s) 120 of the post 72. In some embodiments, the leg portion(s) 124 may extend from the body portion(s) 120 of the post 72 toward a proximal end of the anchor member or braid 70. In some embodiments, the leg portion(s) 124 may be attached to the body portion(s) 120 of the post 72 at the distal end of the body portion(s) 120 of the post 72. In some embodiments, at least part of the leg portion(s) 124 may longitudinally overlap the receiving portion or buckle 76 along a central longitudinal axis of the anchor member or braid 70 in the "deployed" configuration.

In some embodiments, the leg portion(s) 124 may include a free end 126 and a secured end, where the leg portion(s) 124 may be attached to the body portion(s) 120 of the post 72 at the secured end, which may connect directly to the hinge portion(s) 122. In some embodiments, the plurality of leg portions 124 may be joined together at the free end 126. In some embodiments, the plurality of leg portions 124 may be arranged generally parallel to each other. In some embodiments, the free end 126 of the leg portion(s) 124 may be unattached (i.e., not directly attached) to any other structure of the medical implant 16, except for the leg portion 124 and/or the plurality of valve leaflets 68. In other words, in some embodiments, the free end 126 may not be directly attached to any other structure or feature of the medical implant 16 (i.e., the receiving portion or buckle 76, the anchor member or braid 70, etc.). In some embodiments, a distalmost end of the post 72, which in at least some embodiments may be and/or include the hinge portion(s) 122, may be coupled to the distal end of the anchor member or braid 70, such as, for example, by a coupling member such as a suture, filament, wire, or other suitable means. As such, when the post 72 is pulled proximally to engage the receiving portion or buckle 76, the distal end of the anchor member or braid 70 is also pulled proximally relative to the receiving portion or buckle 76, thereby transitioning from the "delivery" configuration toward the "deployed" configuration.

In at least some embodiments, one or more of the plurality of valve leaflets 68 may be attached to the leg portion(s) 124. In some embodiments at least some of the plurality of valve leaflets 68 may extend and/or pass between the plurality of leg portions 124. In some embodiments, at least some of the plurality of valve leaflets 68 may extend and/or pass between two adjacent leg portions 124. In some embodiments, the plurality of valve leaflets 68 may be secured directly to the leg portion(s) 124. In some embodiments, the plurality of valve leaflets 68 may not be directly secured to the body portion(s) 120 and/or the bar portion 96 of the post 72, but is instead coupled to the post 72 via the leg portion(s) 124. In some embodiments, the plurality of valve leaflets 68 may be wrapped around the leg portion(s) 124. In some embodiments, the at least some of the plurality of valve leaflets 68 extending and/or passing between two adjacent leg portions 124 may wrap around the two adjacent leg portions 124. In some embodiments, a distalmost end of the plurality of valve leaflets 68 may be coupled to the distal end of the anchor member or braid 70. In some embodiments, the plurality of valve leaflets 68 may be coupled and/or secured (i.e., to the leg portion(s) 124, to the anchor member or braid 70, and/or back to themselves) using one or more sutures, threads, wires, filaments, or other suitable elements. In some embodiments, the plurality of valve leaflets 68 may be coupled and/or secured (i.e., to the leg portion(s) 124, to the anchor member or braid 70, and/or back to themselves) using an adhesive, a bonding agent, or other suitable securing means. In some embodiments, the plurality of valve leaflets 68 may be coupled and/or secured (i.e., to the leg portion 124, to the anchor member or braid 70, and/or back to themselves) using a fabric, a textile, or other thin flexible material.

In some embodiments, the handle 18 may include a handle housing. A rotatable control knob may be disposed about the handle housing (e.g., at a proximal end of the handle housing) and may be used to move one or more of the components of the medical device system 10 (e.g., outer sheath 12, push-pull rods 84, etc.). A rotatable collar may be disposed about the handle housing. The control knob may be disposed about a proximal portion of the rotatable collar. A slidable door may also be disposed about the handle housing. The slidable door may translate distally to expose a distal portion of the rotatable collar positioned generally under the slidable door. The rotatable collar may be rotated to move one or more components of the medical device system 10 (e.g., push-pull rods 84, pin release mandrel 92, etc.). The handle 18 may also include one or more apertures and/or flush ports that can be used to flush the medical device system 10. In some embodiments, a distal flush port and a proximal flush port may be accessible from the exterior of the handle housing through a distal aperture and a proximal aperture, respectively.

A proximal end of the inner catheter 14 may be attached (e.g., fixedly attached) to an interior body or diverter. The diverter may be attached to a support body. In general, the diverter and/or the support body may have one or more passageways or lumens formed therein. In some embodiments, the actuator elements or push-pull rods 84 and/or the pin release mandrel 92 may extend through respective passageways. Alternatively, the proximal ends of the actuator elements or push-pull rods 84 and/or the pin release mandrel 92 may each be attached to a shaft or hypotube (e.g., solid in cross-section, tubular, etc.), and each of the shafts may extend through the one or more passageways. For example, a first shaft or hypotube and a second shaft or hypotube may extend through the passageways in the diverter, and in some embodiments, the first shaft or hypotube extends through a first passageway and the second shaft or hypotube extends through a second passageway that is separate or distinct from the first passageway. In at least some embodiments, the first shaft is attached to the pin release mandrel 92. In at least some embodiments, the second shaft is attached to the actuator elements or push-pull rods 84. As noted above, in least some embodiments of the medical device system 10, three actuator elements or push-pull rods 84 are utilized. In these embodiments, the three actuator elements or push-pull rods 84 come together (e.g., brought into contact with one another or otherwise brought into relatively close proximity with one another) adjacent to the distal end of the inner catheter 14 and enter the first lumen. At one or more positions along their length, the actuator elements or push-pull rods 84 may be attached to one another. For example, in some embodiments, the actuator elements or push-pull rods 84 may be welded together about 10.16 cm (about 4.00 inches) from their distal ends. In some embodiments, actuator elements or push-pull rods 84 may be welded together proximate their proximal ends in addition to or instead of the distal weld. Proximally thereafter, the actuator elements or push-pull rods 84 may extend to the second shaft.

A hypotube (e.g., a hypotube liner disposed along a guidewire lumen) may extend through the diverter within a passageway therein and then be "diverted" around a portion of the diverter and the support body, and ultimately be extended to a position at the proximal end of the handle 18 so as to provide a user access to the guidewire lumen. The proximal flush port may be disposed on the support body that can be used to flush the lumens of the inner catheter 14 and, for example, may function similarly to the distal flush port.

At their respective proximal ends, the first shaft may be secured to a slider and the second shaft may be secured to a force limiter body. The connections between the various components may include a number of different types of connections including mechanical bonding (e.g., pinning, threading, interference fit, etc.), adhesive bonding, thermal bonding, etc. The slider may be slidable relative to the force limiter body. In some embodiments, the slider may be selectively locked to the force limiter body, thereby preventing relative movement between the slider and the force limiter body. The force limiter body may be secured to a push-pull rod carriage, which may be threaded onto a lead screw. Thus, movement of the lead screw can cause movement of the push-pull rod carriage and the force limiter body and thus, the actuator elements or push-pull rods 84 (via the second shaft).

In general, the force limiter body forms or defines a stop point that provides tactile feedback (e.g., resistance to further rotation of the control knob) to the user indicating that the actuator elements or push-pull rods 84 have been retracted proximally a sufficient distance to lock the posts 72 with the buckles 76. To verify proper locking, a clinician may use an appropriate visualization technique to visualize proper locking (e.g., the relative positioning of the posts 72 and the buckles 76). A chock may be positioned adjacent to the slider to selectively lock the slider to the force limiter body. In order to allow the pin release mandrel 92 to be proximally retracted to pull the pins 88, the chock can be rotated or otherwise moved to a secondary position or configuration. When in this configuration, the chock no longer forms a barrier to further movement of, for example, the slider and the pin release mandrel 92. Accordingly, with the chock no longer acting as an impediment, the slider and the pin release mandrel 92 can be proximally retracted to facilitate deployment of the medical implant 16 by allowing the pins 88 to be pulled.

The handle 18 also includes a rotatable ring with internal teeth that are configured to engage with teeth on a gear coupled to the lead screw. The ring is coupled to the control knob so that rotation of the control knob results in analogous motion of the ring and thus the lead screw.

The handle 18 is generally configured for coordinated movement of multiple structures of the medical device system 10. For example, the handle 18 is configured to allow a user to move the outer sheath 12 (e.g., relative to the inner catheter 14), move the actuator elements or push-pull rods 84, and move the pin release mandrel 92. Moreover, the handle 18 is configured so that the appropriate structure can be moved at the appropriate time during the intervention so that the medical implant 16 can be delivered and released in an efficient manner. Some examples of how the coordinated movement of the medical device system 10 may occur within the handle 18 may be similar to those disclosed in U.S. Patent Application Publication No. US 2010/0280495, the entire disclosure of which is herein incorporated by reference.

To help facilitate the coordinated movement, the handle 18 may include a lost motion barrel. The lost motion barrel is configured to engage a sheath carriage and a push-pull rod carriage and/or screws associated with the sheath and push-pull rod carriages at different times during the intervention to stop motion (e.g., create "lost motion" of the appropriate carriage). For example, in a first position or state for the handle 18, the outer sheath 12 is extended distally relative to the inner catheter 14 (and the handle 18) so as to fully sheath (e.g., contain) the medical implant 16. While in this position, the sheath carriage is positioned adjacent to the distal end of the handle 18. In addition, a rod screw associated with the push-pull rod carriage is extended distally from the push-pull rod carriage and positioned within a lost motion barrel. Upon rotation of the control knob (e.g., in the clockwise direction), the lead screw begins to rotate. Rotation of the lead screw causes the sheath carriage to move along the lead screw in the proximal direction, resulting in proximal movement of the outer sheath 12 (e.g., "unsheathing" the medical implant 16). This initial rotation of the lead screw also causes a rod screw to rotate. This may be because, for example, a knob or projection (not shown) on the rod screw may be engaged with a helical thread disposed along the interior of the lost motion barrel. However, because the rod screw is spaced from the push-pull rod carriage, it does not exert a force onto the push-pull rod carriage. Thus, initial motion of the control knob does not result in movement of the push-pull rod carriage and, instead, only results in translation of the sheath carriage and rotation (and translation) of the rod screw.

Eventually, the rod screw (e.g., the knob formed therein) reaches an essentially linear thread or pathway formed at the end of the lost motion barrel. The linear thread allows the rod screw to translate along the lead screw to a position where the rod screw contacts (e.g., is threaded within and abuts) the push-pull rod carriage. In doing so, the rod screw can contact and move the proximally push-pull carriage. Accordingly, further rotation of the lead screw not only causes the sheath carriage to move proximally but also causes the push-pull rod carriage to move proximally.

When the sheath carriage reaches the lost motion barrel, a sheath carriage screw of the sheath carriage enters the lost motion barrel. This may occur in a manner similar to how the rod screw threads and unthreads with the helical thread formed along the lost motion barrel. For example, while the sheath carriage is translating, the sheath carriage screw may follow an essentially linear thread or pathway formed along or adjacent to the lost motion barrel. Upon reaching the lost motion barrel, the sheath carriage screw (e.g., a knob or projection formed thereon) may shift into engagement with the helical thread within the lost motion barrel and rotate. This rotation "unthreads" the sheath carriage screw from the sheath carriage. Accordingly, additional rotation of the lead screw results in continued proximal movement of the push-pull rod carriage while motion of the sheath carriage ceases.

In at least some embodiments, the lead screw has a plurality of portions, for example a first portion and a second portion, with a differing pitch to its thread. This may allow the sheath and push-pull rod carriages to travel at different rates along the lead screw. For example, the pitch of the lead screw along which the sheath carriage translates may be generally more spaced or slanted than at positions adjacent to the push-pull rod carriage. Accordingly, the coordinated movement of the sheath and push-pull rod carriages also may be configured so that the sheath carriage translates along the lead screw at a greater rate than the push-pull rod carriage. Other configurations are contemplated where the above-mentioned configuration is reversed as well as further configurations where the pitch of the lead screw is essentially constant or includes a number of different pitch regions.

Sufficient proximal retraction of the push-pull rod carriage may result in the actuator elements or push-pull rods 84 being sufficiently retracted so that the posts 72 can engage and lock with the buckles 76. When the clinician is satisfied that locking is complete (e.g., after verification via an appropriate visualization technique), the clinician may proximally retract the pin release mandrel 92 in order to pull the pins 88 from the openings 98 and the elongated apertures or slots in the actuator elements or push-pull rods 84 to release the medical implant 16.

To initiate release of the pins 88, the door may be slid distally along a collar which is positioned on the handle 18. When the door is sufficiently advanced, the door and the collar, together, can be rotated about a longitudinal axis of the handle 18. The push-pull rod carriage may also include a radially-extending proximal flag member. In general, the flag member may be designed as a feature that can prevent the collar from being rotated earlier than desired (and, thus, prevent the pins from being pulled earlier than desired). For example, the flag member may be positioned within and follow a groove along the interior of the collar. While positioned within the groove, the flag member essentially forms a physical barrier that prevents the collar from rotating relative to the handle housing. When the push-pull rod carriage is translated proximally to the back of the handle housing (e.g., when the actuator elements or push-pull rods 84 are proximally retracted so as to lock the posts 72 with the buckles 76), the flag member exits the groove in the collar. Accordingly, the flag member no longer impedes rotation of the collar and, as such, the collar can now be rotated to pull the pins 88.

The collar, via a ring, is associated with a gear engaged with a secondary screw. Notches at a proximal end of the collar engage protrusions on the ring such that rotation of the collar causes corresponding rotation of the ring and thus the secondary screw. The initial rotation of the collar is sufficient to rotate the chock (e.g., via a mechanical interaction between the collar and the chock that causes the chock to shift) from a first configuration where the slider (and, thus, the pin release mandrel 92) is selectively locked to the force limiter body, to a secondary configuration, which permits the slider to translate along the secondary screw as the secondary screw rotates, to proximally retract and pull the pins 88 (e.g., via the pin release mandrel 92). The chock in the first configuration engages a ridge along a top portion of the force limiter body which forms a physical barrier that prevents proximal translation of the slider relative to the force limiter body. When the collar is rotated to shift the chock into the secondary configuration, the slider can translate proximally within a groove disposed in the top portion of the force limiter body, as the collar is rotated about the handle housing to pull the pins 88 from the openings 98 and the elongate apertures or slots in the distal ends of the actuator elements or push-pull rods 84. Once the pins 88 have been removed, the actuator elements or push-pull rods 84 may be withdrawn from the medical implant 16, thereby releasing the implant at the target site (area of interest).

Following release of the medical implant 16, the control knob may be rotated to move the sheath carriage distally within the handle housing, thereby moving the outer sheath 12 distally relative to the inner catheter 14 and the coupler 78 so as to cover or re-sheath the elements of the medical device system 10 disposed at the distal end. The medical device system 10 may then be removed from the patient's anatomy.

The materials that can be used for the various components of the medical device system 10 (and/or other systems disclosed herein) and the various tubular members disclosed herein may include those commonly associated with medical devices. For simplicity purposes, the following discussion makes reference to the outer sheath 12 and/or the inner catheter 14. However, this is not intended to limit the devices and methods described herein, as the discussion may be applied to other similar tubular members and/or components of tubular members or devices disclosed herein, such as, but not limited to, the actuator element or push-pull rod, the unlocking member, the first locking portion, the second locking portion, and/or elements or components thereof.

In some embodiments, the outer sheath 12 and/or the inner catheter 14 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the outer sheath 12 and/or the inner catheter 14 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10 to achieve the same result.

In some embodiments, a degree of Magnetic Resonance Imaging (MRI) compatibility is imparted into the medical device system 10. For example, the outer sheath 12 and the inner catheter 14, or portions thereof, may be made of a material that does not substantially distort the image and create substantial artifacts (i.e., gaps in the image). Certain ferromagnetic materials, for example, may not be suitable because they may create artifacts in an MRI image. The outer sheath 12 and the inner catheter 14, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of the outer sheath 12 and the inner catheter 14 that may define a generally smooth outer surface for the medical device system 10. In other embodiments, however, such a sheath or covering may be absent from a portion of all of the medical device system 10, such that the outer sheath 12 and the inner catheter 14 may form an outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the medical device system 10 (including, for example, the exterior surface of the outer sheath 12 and the inner catheter 14) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of the outer sheath 12 and the inner catheter 14, or other portions of the medical device system 10. Alternatively, the sheath may comprise a lubricious, hydrophilic, protective, or other type of coating. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found, for example, in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

The following documents are herein incorporated by reference in their entirety:

U.S. Patent Application Publication No. US 2007/0112355;

U.S. Patent Application Publication No. US 2010/0219092;

U.S. Patent Application Publication No. US 2010/0280495;

U.S. Patent Application Publication No. US 2011/0257735;

U.S. Patent Application Publication No. US 2013/0123796; and

U.S. Patent Application Publication No. US 2013/0158656.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A valve replacement implant, comprising:
   an expandable anchor member having a proximal end and a distal end, the anchor member being actuatable between a delivery configuration and a deployed configuration;
   a plurality of locking mechanisms configured to secure the anchor member in the deployed configuration, each locking mechanism including:
      an axially movable post including a leg portion extending radially inwardly therefrom at an acute angle; and
      a receiving portion fixed to the anchor member, the receiving portion being configured to slidably receive the post;
   a plurality of valve leaflets disposed within a central lumen of the anchor member, the plurality of valve leaflets being secured to the leg portions of the plurality of locking mechanisms;
   wherein the plurality of locking mechanisms is releasably attached to a delivery device;
   wherein the anchor member is actuated between the delivery configuration and the deployed configuration by translating the post proximally relative to the receiving portion.

2. The valve replacement implant of claim 1, wherein the leg portion extends from the post toward the proximal end.

3. The valve replacement implant of claim 1, wherein the leg portion is attached to the post at a distal end of the post.

4. The valve replacement implant of claim 1, wherein the leg portion is flexibly attached to the post.

5. The valve replacement implant of claim 1, wherein the leg portion includes a free end and a secured end, the leg portion being attached to the post at the secured end.

6. The valve replacement implant of claim 5, wherein the free end is unattached to any other structure except through the leg portion.

7. The valve replacement implant of claim 1, wherein at least part of the leg portion longitudinally overlaps the receiving portion along a central longitudinal axis of the anchor member in the deployed configuration.

8. The valve replacement implant of claim 1, wherein the plurality of valve leaflets is secured directly to the leg portions.

9. The valve replacement implant of claim 1, wherein the plurality of valve leaflets is not directly secured to the posts.

10. The valve replacement implant of claim 1, wherein the post includes two leg portions extending inwardly therefrom.

11. The valve replacement implant of claim 10, wherein the two leg portions are joined together at a free end opposite the post.

12. The valve replacement implant of claim 10, wherein the two leg portions are arranged generally parallel to each other.

13. The valve replacement implant of claim 10, wherein at least some of the plurality of valve leaflets pass between the two leg portions.

14. The valve replacement implant of claim 13, wherein the at least some of the plurality of valve leaflets passing between the two leg portions wrap around the two leg portions.

15. The valve replacement implant of claim 14, wherein the at least some of the plurality of valve leaflets passing between the two leg portions and wrapping around the two leg portions are secured back to themselves.

16. The valve replacement implant of claim 15, wherein the at least some of the plurality of valve leaflets are secured back to themselves using one or more sutures.

17. The valve replacement implant of claim 15, wherein the at least some of the plurality of valve leaflets are secured back to themselves using an adhesive.

18. The valve replacement implant of claim 1, wherein a distalmost end of the post is coupled to the distal end of the anchor member.

19. The valve replacement implant of claim 1, wherein a distalmost end of the plurality of valve leaflets is coupled to the distal end of the anchor member.

* * * * *